US010213447B2

(12) United States Patent
Ngo et al.

(10) Patent No.: US 10,213,447 B2
(45) Date of Patent: Feb. 26, 2019

(54) PREPARATION OF ACETATE SALT COMPOSITIONS OF PHARMACEUTICAL AGENTS

(71) Applicant: The Curators of the University of Missouri, Columbia, MO (US)

(72) Inventors: Albert N. Ngo, Kansas City, MO (US); Bi-Botti C. Youan, Kansas City, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/178,938

(22) Filed: Jun. 10, 2016

(65) Prior Publication Data

US 2016/0361327 A1    Dec. 15, 2016

Related U.S. Application Data

(60) Provisional application No. 62/173,772, filed on Jun. 10, 2015.

(51) Int. Cl.
| | | |
|---|---|---|
| *A61K 9/08* | (2006.01) |
| *A61K 9/16* | (2006.01) |
| *A61K 9/19* | (2006.01) |
| *A61K 9/50* | (2006.01) |
| *A61K 31/675* | (2006.01) |

(52) U.S. Cl.
CPC ............. *A61K 31/675* (2013.01); *A61K 9/08* (2013.01); *A61K 9/1617* (2013.01); *A61K 9/1682* (2013.01); *A61K 9/19* (2013.01); *A61K 9/5036* (2013.01)

(58) Field of Classification Search
CPC ...... A61K 31/675; A61K 9/08; A61K 9/1617; A61K 9/1682; A61K 9/19; A61K 9/5036
See application file for complete search history.

(56) References Cited

U.S. PATENT DOCUMENTS

| 2,895,990 | A | * | 7/1959 | Larrison | ............... | C07C 51/412 |
| | | | | | | 562/606 |
| 2009/0035356 | A1 | | 2/2009 | Bui-Khac et al. | | |
| 2012/0027833 | A1 | | 2/2012 | Zilberman | | |
| 2012/0258176 | A1 | | 10/2012 | Sung et al. | | |
| 2013/0323179 | A1 | * | 12/2013 | Popov | .................. | A61K 9/5031 |
| | | | | | | 424/9.6 |

FOREIGN PATENT DOCUMENTS

WO    2016201213 A1    12/2016

OTHER PUBLICATIONS

Ruiz-Caro et al., "Characterization and Dissolution Study of Chitosan Freeze-Dried Systems for Drug Controlled Release", Molecules, vol. 14, pp. 4370-4386. (Year: 2009).*
Zinc Acetate. In Hawley's Condensed Chemical Dictionary, R. J. Lewis (Ed.), 2007. (Year: 2007).*
Divya et al., "Design, Formulation and Characterization of Tenofovir Microemulsion as Oral Drug Delivery", 2014, International Journal of Pharmacy Review and Research, vol. 4, issue 1, pp. 1-5. (Year: 2014).*
Veyries et al., "Controlled release of vancomycin from Poloxamer 407 gels", 1999, International Journal of Pharmaceutics, vol. 192, pp. 183-193. (Year: 1999).*
Shalmashi et al., "Solubility of Caffeine in Water, Ethyl Acetate, Ethanol, Carbon Tetrachloride, Methanol, Chloroform, Dichloromethane, and Acetone Between 298 and 323 K", 2010, Latin American Applied Research, vol. 40, No. 3, pp. 283-285. ( Year: 2010).*
Ruiz-Caro, Robert, Veiga-Ochoa, Maria Dolores. Characterization and Dissolution Study of Chitosan Freeze-Dried Systems for Drug Controlled Release. Molecules. 14:4370-4386 (2009).
Mi, Fwu-Long, Shyu, Shin-Shing, Wong, Tsung-Bi, Jang, Shiang-Fang, Lee, Sung-Tao, Lu, Kai-Tai. Chitosan-Polyelectrolyte Complexation for the Preparation of Gel Beads and Controlled Release of Anticancer Drug. II. Effect of pH-Dependent Ionic Crosslinking or Interpolymer Complex Using Tripolyphosphate or Polyphosphate as Reagent. Journal of Applied Polymer Science. 74:1093-1107 (1999).
Hu, Wenting, Ding, Liping, Cao, Jianhua, Liu, Lili, Wei, Yuting, Fang, Yu. Protein Binding-Induced Surfactant Aggregation Variation: A New Strategy of Developing Fluorescent Aqueous-Sensor for Proteins. ACS Applied Materials & Interfaces. 7:4728-4736 (2015).
Poth Nils, Seiffart, Virginia, Gross, Gerhard, Menzel, Dempwolf, Wibke. Biodegradable Chitosan Nanoparticle Coatings on Titanium for the Delivery of BMP-2. Biomolecules. 5:3-19 (2015).
International Search Report, PCT/US16/36871, dated Oct. 28, 2016.
Y.L. Lee, T. Cesario, J. Owens, E. Shanbrom, and L.D. Thrupp. Antibacterial activity of citrate and acetate. Nutrition. 18:665-666 (2002).
G. Frech, L.V. Allen, Jr., M.L. Stiles, and R.S. Levinson. Sodium acetate as a preservative in protein hydrolysate solutions. American journal of hospital pharmacy. 36:1672-1675 (1979).
H. Karaca, M.B. Perez-Gaga, V. Taberner, and L. Palou. Evaluating food additives as antifungal agents against Monilinia fructicola in vitro and in hydroxypropyl methylcellulose-lipid composite edible coatings for plums. International journal of food microbiology. 179:72-79 (2014).
C. Costa, A. Conte, and M.A. Del Nobile. Effective preservation techniques to prolong the shelf life of ready-to-eat oysters. J Sci Food Agric. 94:2661-2667 (2014).
D. Fong, M.B. Ariganello, J. Girard-Lauziere, and C.D. Hoemann. Biodegradable chitosan microparticles induce delayed STAT-1 activation and lead to distinct cytokine responses in differentially polarized human macrophages in vitro. Acta biomaterialia(2014).

(Continued)

*Primary Examiner* — Michael B. Pallay
(74) *Attorney, Agent, or Firm* — Brannon Sowers & Cracraft PC

(57) ABSTRACT

Processes for preparing compositions comprising pharmaceutical agents encapsulated in nanoparticles which provide improved physicochemical and biological properties are described. Also described are compositions comprising water soluble pharmaceutical agents which provide extended release of the pharmaceutical agent. Processes are described for preparing compositions which increase the aqueous availability of compounds with low water solubility.

12 Claims, 18 Drawing Sheets

(56) References Cited

OTHER PUBLICATIONS

A. Smith, M. Perelman, and M. Hinchcliffe. Chitosan: a promising safe and immune-enhancing adjuvant for intranasal vaccines. Human vaccines & immunotherapeutics. 10:797-807 (2014).

H. Zheng, C. Tang, and C. Yin. Exploring advantages/disadvantages and improvements in overcoming gene delivery barriers of amino Acid modified trimethylated chitosan. Pharm Res. 32:2038-2050 (2015).

J. Meng, T.F. Sturgis, and B.B. Youan. Engineering tenofovir loaded chitosan nanoparticles to maximize microbicide mucoadhesion. Eur J Pharm Sci. 44:57-67 (2011).

A.N. Ngo, M.J. Ezoulin, I. Youm, and B.B. Youan. Optimal Concentration of 2,2,2-Trichloroacetic Acid for Protein Precipitation Based on Response Surface Methodology. Journal of analytical & bioanalytical techniques. 5:(2014).

A.A. Date and C.J. Destache, A review of nanotechnological approaches for the prophylaxis of HIV/AIDS, Biomaterials. 34:6202-6228 (2013).

A. Kapoor, R. Sharma, P. Sharma, P. Gupta. BCS Classification System: Benchmark for Solubility and Permeability. Indo American Journal of Pharmaceutical Research. 4:(2014).

X. Wang, C. Zheng, Z. Wu, D. Teng, X. Zhang, Z. Wang, and C. Li. Chitosan-NAC nanoparticles as a vehicle for nasal absorption enhancement of insulin. Journal of biomedical materials research Part B, Applied biomaterials. 88:150-161 (2009).

A. Rampino, M. Borgogna, P. Blasi, B. Bellich, and A. Cesaro. Chitosan nanoparticles: preparation, size evolution and stability. Int J Pharm. 455:219-228 (2013).

M. Dionisio, C. Cordeiro, C. Remunan-Lopez, B. Seijo, A.M. Rosa da Costa, and A. Grenha. Pullulan-based nanoparticles as carriers for transmucosal protein delivery. Eur J Pharm Sci. 50:102-113 (2013).

B. D. Cullity and S.R. Stock. Elements X-ray Diffraction. Book, ISBN 0-12-352651-5:309 (2001).

J.S. Fritz. Titration of Bases in Nonaqueous Solvents. Analytical Chemistry. 22:1028-1029 (1950).

G. A. Harlow and D.B. Bruss. Titration of Weak Acids in Nonaqueous Solvents: Potentiometric Studies in Inert Solvents. Analytical Chemistry. 30:1833-1836 (1958).

P. Costa and J.M. Sousa Lobo. Modeling and comparison of dissolution profiles. Eur J Pharm Sci. 13:123-133 (2001).

A.S. Wadajkar, T. Kadapure, Y. Zhang, W. Cui, K.T. Nguyen, and J. Yang. Dual-imaging enabled cancer-targeting nanoparticles. Adv Healthc Mater. 1:450-456 (2012).

S.K. Panda, S. Kumar, N.C. Tupperwar, T. Vaidya, A. George, S. Rath, V. Bal, and B. Ravindran. Chitohexaose activates macrophages by alternate pathway through TLR4 and blocks endotoxemia. PLoS Pathog. 8:e1002717 (2012).

S. Lanone, F. Rogerieux, J. Geys, A. Dupont, E. Maillot-Marechal, J. Boczkowski, G. Lacroix, and P. Hoet. Comparative toxicity of 24 manufactured nanoparticles in human alveolar epithelial and macrophage cell lines. Part Fibre Toxicol. 6:14 (2009).

E. Borenfreund and J.A. Puerner. Toxicity determined in vitro by morphological alterations and neutral red absorption. Toxicol Lett. 24:119-124 (1985).

E. Vega-Avila and M.K. Pugsley. An overview of calorimetric assay methods used to assess survival or proliferation of mammalian cells. Proc West Pharmacol Soc. 54:10-14 (2011).

L. Connelly, M. Palacios-Callender, C. Ameixa, S. Moncada, and A.J. Hobbs. Biphasic regulation of NF-kappa B activity underlies the pro- and anti-inflammatory actions of nitric oxide. J Immunol. 166:3873-3881 (2001).

I.D. Kim and B.J. Ha. Paeoniflorin protects RAW 264.7 macrophages from LPS-induced cytotoxicity and genotoxicity. Toxicol In Vitro. 23:1014-1019 (2009).

A. Introini, C. Vanpouille, A. Lisco, J.C. Grivel, and L. Margolis. Interleukin-7 facilitates HIV-1 transmission to cervico-vaginal tissue ex vivo. PLoS pathogens. 9:e1003148 (2013).

E.N. Koukaras, S.A. Papadimitriou, D.N. Bikiaris, and G.E. Froudakis. Insight on the formation of chitosan nanoparticles through ionotropic gelation with tripolyphosphate. Molecular pharmaceutics. 9:2856-2862 (2012).

M. H. Ki, J. E. Kim, Y. N. Lee, S. M. Noh, S. W. An, H. J. Cho, and D. D. Kim. Chitosan-based hybrid nanocomplex for siRNA delivery and its application for cancer therapy. Pharm Res. 31:3323-3334 (2014).

C. Giovino, I. Ayensu, J. Tetteh, and J.S. Boateng. An integrated buccal delivery system combining chitosan films impregnated with peptide loaded PEG-b-PLA nanoparticles. Colloids and surfaces B, Biointerfaces. 112:9-15 (2013).

Y. Zu, Q. Zhao, X. Zhao, S. Zu, and L. Meng. Process optimization for the preparation of oligomycin-loaded folate-conjugated chitosan nanoparticles as a tumor-targeted drug delivery system using a two-level factorial design method. International journal of nanomedicine. 6:3429-3441 (2011).

J. Cho, M.C. Heuzey, A. Begin, and P.J. Carreau. Physical gelation of chitosan in the presence of beta-glycerophosphate: the effect of temperature. Biomacromolecules. 6:3267-3275 (2005).

P.D. Constable. Acid-base assessment: when and how to apply the Henderson-Hasselbalch equation and strong ion difference theory. The Veterinary clinics of North America Food animal practice. 30:295-316, v (2014).

S. Magder and A. Emami. Practical approach to physical-chemical Acid-base management. Stewart at the bedside. Annals of the American Thoracic Society. 12:111-117 (2015).

T. C. Padhiyar and S. B. Thakore. Recovery of Acetic Acid From Effluent via Freeze Crystallization. Internationnal Journal of Scientific Engineering and Technology. 2:211-215 (2013).

P. Atkins and J. de Paula, Atkin's Physical Chemistry, ninth edition. Book, ISBN 978-0-19-954337-3:196 (2010).

F. A. Miller, D. W. Mayo, R. W. Hannah. Course notes on the interpretation of Infrared and Raman Spectra. Wiley&Sons Publication:210-213 (2004).

M. Currie, M. J. Barrow, K. W. Muir, J. C. Speakman and D. N. J. White. Crystal Structures of Some Acid Salts of Monobasic Acids. Part XVII. Structure of Sodium Hydrogen Diacetate, redetermined by Neutron Diffraction. Journal of Chemical Society Perkin 2:15-17.

T.S. Cameron. The crystal structure of sodium acetate trihydrate. Acta Crystallographica Section B. 32:87-90 (1976).

B.D. Cullity and S.R. Stock. Elements X-Ray Diffraction Book, ISBN 0-201-61091-4. 3 296 (2001).

M.D. Chavanpatil, P. Jain, S. Chaudhari, R. Shear, and P.R. Vavia. Novel sustained release, swellable and bioadhesive gastroretentive drug delivery system for ofloxacin. Int J Pharm. 316:86-92 (2006).

J. Lopez-Garcia, M. Lehocky, P. Humpolicek, and P. Saha. HaCaT Keratinocytes Response on Antimicrobial Atelocollagen Substrates: Extent of Cytotoxicity, Cell Viability and Proliferation. Journal of functional biomaterials. 5:4344.

U. Stange, C. Fuhrling, and H. Gieseler. T-57 (2014). taste masking of naproxen sodium granules by fluid-bed coating. Pharmaceutical development and technology. 19:137-147 (2014).

S. Joshi and H.U. Petereit. Film coatings for taste masking and moisture protection. Int J Pharm. 457:395-406 (2013).

S.T. Gunawan, K. Liang, G.K. Such, A.P. Johnston, M.K. Leung, J. Cui, and F. Caruso. Engineering enzyme-cleavable hybrid click capsules with a pH-sheddable coating for intracellular degradation. Small. 10:4080-4086 (2014).

A.M. Elbarbary and T.B. Mostafa. Effect of gamma-rays on carboxymethyl chitosan for use as antioxidant and preservative coating for peach fruit. Carbohydrate polymers. 104:109-117 (2014).

* cited by examiner

US 10,213,447 B2

PREPARATION OF ACETATE SALT COMPOSITIONS OF PHARMACEUTICAL AGENTS

CROSS-REFERENCE TO RELATED APPLICATIONS

This application claims the benefit under 35 USC § 119(e) of U.S. Provisional Application No. 62/173,772 filed on Jun. 10, 2015, the entire disclosure of which is herein incorporated by reference.

GOVERNMENT RIGHTS

This invention was made with Government support under Grant No. R01 AI087304 awarded by the National Institute of Allergic and Infectious Diseases. The Government has certain rights in the invention.

FIELD

Described herein are processes for preparing pharmaceutical agents encapsulated in nanoparticles with improved physicochemical and biological properties. Also described are extended release formulations for water soluble pharmaceutical agents. Processes are also described for increasing the aqueous availability of bioactive compounds.

BACKGROUND AND SUMMARY

Sodium acetate (SA), is approved by European food control authorities, and is an edible salt that is added to food as a seasoning. It has a wide range of applications. Firstly, it is used as antibacterial additive and preservative in food compounds; it is an inhibitor of gram-negative bacteria, and fungi that grow in food. Secondly, oysters shelf life can be extend through dipping in sodium acetate. Sodium acetate is generally prepared by mixing an aqueous solution of sodium carbonate or hydroxide with an aqueous solution of acetic acid. The recovery of sodium acetate, in this aqueous solution, is generally either by crystallization or evaporation using techniques such as spray drying (U.S. Pat. No. 2,895,990). Beside its widespread use in food industry, up-to-day, little is known about the coating property of sodium acetate for pharmaceutical nano-formulations.

Chitosan is a polysaccharide obtained from the deacetylation of chitin and have been used as a nanocarrier for novel drug delivery system because of its biodegradable and biocompatible properties (H. Zheng, et al., Pharm Res. 32:2038-2050 (2015)). Among chitosan based nanocarriers, chitosan crosslinked with polyanion triphosphate (TPP) based nanoparticles (NPs) have been widely used for the nano-encapsulation of HIV/AIDS microbicide such as tenofovir (TFV). The solubility in water, log P and and its oral bioavailability of TFV are 13.4 mg/mL, −1.1, and, 25-39%, respectively. TFV is a BCS class III drug (A. A. Dateand, et al., Biomaterials. 34:6202-6228 (2013)).

However, the nano-encapsulation process using chitosan-TPP ionic gelation, and a water soluble drug such as TFV, has several limitations. Firstly, the encapsulation efficiency (EE %) of a water soluble drug, such as TFV is typically very low. For instance, Meng, et al. encapsulated only 5.83% of TFV in chitosan NPs. Secondly, chitosan NPs exhibits an initial burst release leading to a failure to sustain release, and protect drugs. Thirdly, the freeze drying process is not effective for chitosan based NPs in absence of cryoprotectant. This leads to the aggregation of NPs.

Therefore, there is a need to develop a new and modified in situ formation of sodium acetate, which can be used to uniformly coat pharmaceutically loaded NPs (such as chitosan NPs) and dramatically increase the physicochemical properties of the NPs (e.g. improvement of the freeze drying process, EE %, non-aggregation of NPs without the use of cryoprotectant, physical stability, and sustained drug release profile).

This invention provides a series of sodium-acetate-coated pharmaceutically-loaded NPs. This invention further provides a new and improved in situ formation of sodium acetate, which can be used to uniformly coat pharmaceutically loaded NPs (such as chitosan NPs) and dramatically increase the physicochemical properties of the NPs.

According to one embodiment of the invention, the inventive method comprises the steps of i) generating in situ sodium acetate from half neutralization of acetic acid with sodium hydroxide, and ii) coating pharmaceutically loaded NPs during freeze-drying process.

BRIEF DESCRIPTION OF THE DRAWINGS

The drawings described herein are for illustration purposes only and are not intended to limit the scope of the present teachings in any way.

Corresponding reference numerals indicate corresponding parts throughout the several views of drawings.

DETAILED DESCRIPTION

Figure 1A:
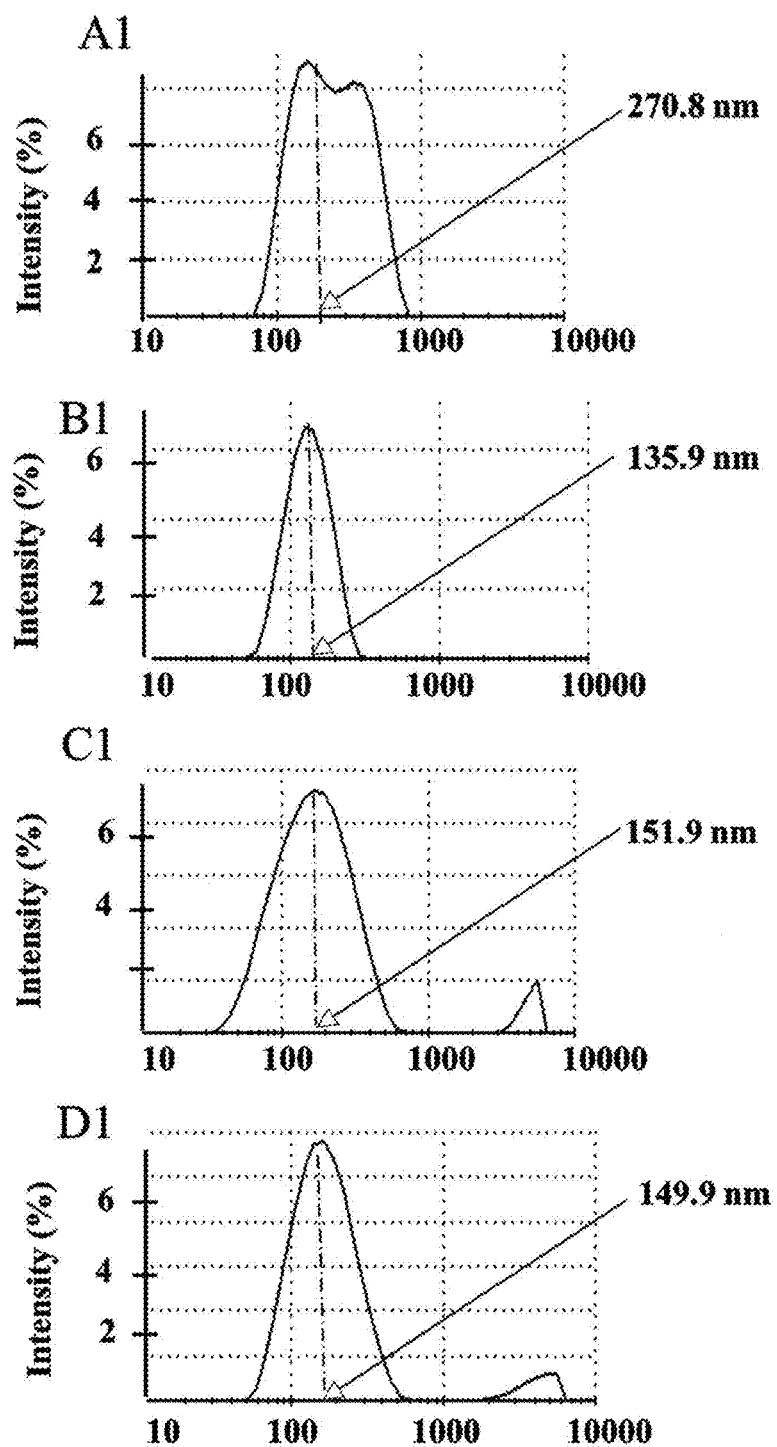
FIG. 1A. Particle size distributions by dynamic light scattering of fresh chitosan NPs (A1, B1, C1, and D1) for blank formulation, F1, F2 and F3 formulation respectively.

The following description is intended to be exemplary in nature and is in no way intended to limit the present teachings, application, or uses. Throughout this specification, like reference numerals will be used to refer to like elements.

Described herein are a series of sodium acetate-coated pharmaceutically-loaded NPs and a new process for the in situ formation of sodium acetate. Described herein are SA-coated NPs and in situ fabrication methods thereof that can be used to uniformly coat pharmaceutically loaded NPs (such as chitosan NPs) improving the physicochemical properties of the resulting NPs. In embodiments described herein, processes which employ sodium acetate to coat in situ pharmaceutical NPs during the formation phase have been discovered herein to provide a unique and uniform coating of the nano-formulation. Described herein are processes resulting in improved encapsulation efficiency and loading efficiency of pharmaceutical agents in NPs. Use of the processes described herein prevents or lessens aggregation of the NPs. It is appreciated that the NPs (core-shell NPs) prepared by the processes described herein may be used for i) masking taste and moisture protection of pharmaceutical agents, ii) preventing enzyme degradation encapsulated compounds, iii) increasing the shelf-life of the pharmaceutical agent, and iv) controlling and sustaining release of a bio-active agent in a biological matrix.

Sodium acetate (SA), is approved by European food control authorities, and is an edible salt that is added to food as a seasoning. It has a wide range of applications. It is used as antibacterial additive and preservative in food compound; it is a inhibitor of gram-negative bacteria, and fungi that grow in food (Y. L. Lee, et al., Nutrition. 18:665-666 (2002); G. Frech, et al., American Journal of Hospital Pharmacy. 36:1672-1675 (1979); H. Karaca, et al., International Journal of Food Microbiology. 179:72-79 (2014). For example, the shelf-life of oysters can be extend through dipping in sodium acetate (C. Costa, et al., J Sci. Food Agric. 94:2661-2667 (2014)). Despite its widespread use in the indstry of food, little was known about the coating property of sodium acetate for pharmaceutical nanoformulations.

Chitosan is a amino polysaccharide obtained from the deacetylation of chitin and is widely used as a nanocarrier for novel drug delivery system because it is biodegradable and safe to use and has immune adjuvant properties (D. Fong, et al., Acta Biomaterialia (2014); A. Smith, et al., Human Vaccines & Immunotherapeutics. 10:797-807 (2014)). Among chitosan based nanocarriers, chitosan cross-linked with polyanion triphosphate (TPP) based nanoparticles (NPs) are widely used for the nanoencapsulation of HIV microbicides such as tenofovir (TFV) (J. Meng, et al., Eur J Pharm Sci. 44:57-67 (2011); A. N. Ngo, et al., Journal of Analytical & Bioanalytical Techniques. 5: (2014)). TFV has a solubility in water of 13.4 mg/mL. and BCS class III drug (A. Kapoor, et al., Indo American Journal of Pharmaceutical Research. 4:(2014)). However, the nano-encapsulation process using chitosan-TPP ionic gelation, and a water soluble drug such as tenofovir (TFV), has several limitations. Firstly, the encapsulation efficiency (EE %) of a water soluble drug, such as TFV is typically very low. For instance, Meng, et al. succeeded in encapsulating only 5.83% of TFV in chitosan NPs (Meng, 2011). Secondly, chitosan NPs exhibits an initial burst release (X. Wang, et al., Journal of biomedical materials research Part B, Applied biomaterials. 88:150-161 (2009)) leading to a failure to yield a sustained release, and to protect the drug. Thirdly, the freeze drying process is not effective for chitosan based NPs in absence of cryoprotectant. Not using a cryoprotectant during freeze drying of chitosan based NPs leads to the aggregation of the NPs (A. Rampino, et al., Int J Pharm. 455:219-228 (2013); M. Dionisio, et al., Eur J Pharm Sci. 50:102-113 (2013).).

Described herein is the surprising discovery that in situ formation of sodium acetate can be used to uniformly coat NPs and improve their physicochemical properties (e.g. loading, EE %, improvement of the freeze drying process, safety, control of aggregation, sustained drug release) and biological properties (e.g. safety). The NPs described herein have been characterized by several physicochemical means (e.g. particle size, EE %, zeta potential, Fourier transform infrared spectroscopy (FTIR), X-ray powder diffractometry (XRD) and transmission electron microscopy (TEM)), and characterized by in vitro cell culture for cytotoxicity assessment (e.g. Assessment of cell membrane integrity, mitochondrial activity, assessment of nitric oxide, and cytokine production.

In one embodiment sodium acetate (SA) is used to coat chitosan NPs resulting in improved physico chemical and safety properties of the nanocarriers. Imaging (TEM), spectrum analysis (FTIR), and XRD pattern of the NPs appear to be consistent with the formation of SA-coated NPs. It is believed that the non-aqueous titration of and melting point assessment of the pure salt prepared from acetic acid aqueous solution, using the processes described herein supports the nature of the salt coating the NPs.

In another embodiment an acetate salt is used to enhance the water solubility of a compound with low water solubility. It is appreciated that water solubility of compounds may vary with pH. As used herein, water solubility of a compound generally means water solubility at about pH 6 to about pH 8, unless otherwise stated. In another embodiment, the compound in any of the embodiments described herein has a water solubility of about 1 mg/mL to about 500 µg/mL, of about 400 µg/mL to about 300 µg/mL, of about 300 µg/mL to about 200 µg/mL, of about 200 µg/mL to about 100 µg/mL, of about 100 µg/mL to about 50 µg/mL, of about 50 µg/mL to about 25 µg/mL, of about 25 µg/mL to about 10 µg/mL, or of about 10 µg/mL to about 1 µg/mL.

In another embodiment the acetate salt is used to enhance the water solubility of a compound with a log P value of about 1 to about 2, from about 2 to about 3, from about 3 to about 4, from about 4 to about 5, or from about 5 to about 8.

In any of the embodiments described herein, the compound with low water solubility may be a bioactive compound.

In any of the processes or compositions described herein the acetate salt is one or more acetate salts selected from the group consisting of LiOAc, NaOAc, KOAc, CsOAc, Mg(OAc)2, Ca(OAc)2, Ba(OAc)2, Zn(OAc)2, and Al(OAc)3. In any of the processes or compositions described herein the acetate salt may be formed by treating acetic acid or a solution of acetic acid with a base containing the appropriate counter ion, (e.g. lithium hydroxide, sodium hydroxide, potassium hydroxide, magnesium hydroxide or oxide, calcium hydroxide or oxide, and the like). In another embodiment, in any of the processes or compostions described herein the acetate salt is sodium acetate.

Several non-limiting, illustrative embodiments of the invention are described by the following clauses:

1. A process for improving the aqueous availability in a first aqueous solution of a material with low water solubility, the process comprising:
   (a) forming a second aqueous mixture comprising the material and one or more acetate salts selected from the group consisting of LiOAc, NaOAc, KOAc, CsOAc, Mg(OAc)$_2$, Ca(OAc)$_2$, Ba(OAc)$_2$, Zn(OAc)$_2$, and Al(OAc)$_3$; and
   (b) freeze drying the second aqueous mixture from (b) to yield a solid wherein the material has improved aqueous availability when the solid is mixed with the first aqueous solution.

2. The process of clause 1 wherein the improved availability is improved dispersion of the material in the first aqueous solution.

3. The process of clause 1 wherein the improved aqueous availability is improved solubility of the material in the first aqueous solution.

4. The process of any one of clauses 1 to 3 wherein the material comprises a bioactive compound.

5. The process of any one of the preceding clauses wherein the bioactive material comprises a bioactive compound and a biodegradable polymer.

6. The process of any one of the preceding clauses the bioactive compound is a pharmaceutical agent.

7. The process of any one of clauses 1 to 5 wherein the bioactive compound is a flavoring agent or a fragrance.

8. The process of any one of clauses 1 to 5 wherein the bioactive compound is an agricultural pesticide selected from the group consisting of rodenticides, insecticides, herbicides, fungicides, and nematicides.

9. The process of any one of the preceding clauses wherein the biodegradable polymer is selected from the group consisting of poly(L-lactide) (PLLA), poly(D,L-lactide) (PDLLA), poly(lactic-co-glycolic acid) (PLGA), (poly)caprolactone (PCL), and chitosan.

10. The process of any one of the preceding clauses wherein the biodegradable polymer is chitosan.

11. The process of any one of the preceding clauses where the acetate salt is LiOAc, NaOAc, KOAc, CsOAc, or any combination thereof.

12. The process of any one of the preceding clauses where the acetate salt is NaOAc.

13. The process of any one of clauses 1 to 6 or 9 to 12 wherein the pharmaceutical agent is selected from the group consisting of antibacterials, antivirals, and cancer drugs.

14. The process of any one of clauses 1 to 6 or 9 to 13 wherein the pharmaceutical agent is a cancer drug.

15. The process of any one of clauses 1 to 6 or 9 to 14 wherein the pharmaceutical agent is doxetaxel.

16. The process of any one of the preceding clauses wherein the bioactive agent has a water solubility of about 1 mg/mL to about 500 µg/mL, of about 400 µg/mL to about 300 µg/mL, of about 300 µg/mL to about 200 µg/mL, of about 200 µg/mL to about 100 µg/mL, of about 100 µg/mL to about 50 µg/mL, of about 50 µg/mL to about 25 µg/mL, of about 25 µg/mL to about 10 µg/mL, or of about 10 µg/mL to about 1 µg/mL 17. The process of any one of the preceding clauses wherein the bioactive compound has a log P value of about 1 to about 2, from about 2 to about 3, from about 3 to about 4, from about 4 to about 5, or from about 5 to about 8.

18. The process of any one of the preceding clauses wherein the bioactive compound is encapsulated by the biodegradable polymer.

19. The process of clause 18 wherein the bioactive compound has a water solubility about 5 mg/mL to about 20 mg/mL and the biodegradable polymer is chitosan.

20. A composition comprising a bioactive material prepared by the process of any one of the preceding clause.

21 A process for preparing an extended release formulation for a bioactive compound, the process comprising the steps of;
   (a) preparing a first solution comprising a biodegradable polymer and acetic acid; and
   (b) raising the pH of the first solution to a range of about 4.65 to about 4.85 by adding a solution of sodium hydroxide; and
   (c) preparing a second solution comprising sodium triphosphate and the pharmaceutical agent where the second solution has a pH in the range of about 5.55 to about 5.65; and
   (d) mixing the first solution from (b) with the second solution from (c) to form a third solution; and
   (e) freeze-drying the third solution yielding the extended release formulation.

22. An extended release formulation of a bioactive compound prepared by the process of clause 21.

23. The process or formulation of clause 21 or 22 wherein the bioactive compound has a water solubility of from about 1 mg/mL to about 5 mg/mL, about 5 mg/mL to about 20 mg/mL, from about 10 mg/mL to about 20 mg/mL, from about 10 mg/mL to about 15 mg/mL, from about 5 mg/mL to about 10 mg/mL, from about 5 mg/mL to about 15 mg/mL, from about 0.5 mg/mL to about 5 mg/mL, from about 1 mg/mL to about 5 mg/mL, from about 2.5 mg/mL to about 5 mg/mL, or from about 10 mg/mL to about 50 mg/mL.

24. The process or formulation of any one of clauses 21 to 23 wherein the bioactive compound has a water solubility of from about 10 mg/mL to about 20 mg/mL.

25. The process or formulation of any one of clauses 21 to 24 wherein the bioactive compound has a water solubility of from about 12 mg/mL to about 16 mg/mL.

26. The process or formulation of any one of clauses 21 to 25 wherein the biodegradable polymer is chitosan.

27. The process or formulation of any one of the clauses 21 to 26 wherein the log P of the bioactive compound is from about −2 to about −1, about −2 to about 0, or about −2 to about 1.

28. The process or formulation of any one of the clauses 21 to 27 wherein the log P of the bioactive compound is from about −2 to about −1.

29. The process or formulation of any one of clauses 21 to 28 wherein the bioactive compound is an antiviral.

30. The process or formulation of any one of clauses 21 to 29 wherein the bioactive compound is tenofovir.

31. The process or formulation of any one of clauses 21 to 30 wherein the extended release formulation is in the form of sodium acetate coated nanoparticles of the biodegradable polymer containing the bioactive compound.

32. The process or formulation of any one of clauses 21 to 31 wherein the extended release formulation is in the form of sodium acetate coated nanoparticles of the biodegradable polymer containing the bioactive compound where the nanoparticles have a particle size of about 100 nm to about 500 nm, about 150 nm to about 450 nm or about 150 nm to about 400 nm.

33. The process or formulation of any one of clauses 21 to 32 wherein the extended release formulation is in the form of sodium acetate coated nanoparticles of the biodegradable polymer containing the bioactive compound where the nanoparticles have a zeta-potential in the range of about 4.0 eV to about −1.0 eV, about 3.0 eV to about 0.0 eV, or about 2.0 eV to about 0.0 eV.

34. The process or formulation of any one of clauses 21 to 33 wherein the sodium acetate coated nanoparticles of the biodegradable polymer containing the bioactive compound have a shell core structure.

35. The process or formulation of clause 34 wherein the shell portion of the shell core structure consists essentially of sodium acetate.

In reciting the foregoing collection of clauses, it is to be understood that all possible combinations of features, and all possible subgenera and sub-combinations are described.

Chitosan NPs are usually prepared after protonation of chitosan polymer in acetic acid aqueous solution followed by a straightforward addition of aqueous solution of TPP (N. Poth, et al., Biomolecules. 5:3-19 (2015); E. Koukaras, et al., Molecular pharmaceutics. 9:2856-2862 (2012); M. Ki, et al., Pharm Res. 31:3323-3334 (2014)). In this common method of ionic gelation, the final solution not only did not contain enough of both sodium, and acetate ion in the medium. In addition, in this classic process of ionic gelation, chitosan NPs typically aggregate during the freeze drying process, if no cryoprotectant is used (C. Giovino, et al., Colloids and surfaces B, Biointerfaces. 112:9-15 (2013); Y. Zu, et al., International journal of nanomedicine. 6:3429-3441 (2011)). NPs comprising other biodegradable polymers can be made by methods well-known to those skilled in the art of formulating bioactive materials.

Described herein are processes for preparing NPs useful for encapsulation of a small water-soluble molecule drug or pharmaceutical agent such as TFV. It was not possible to efficiently encapsulate TFV into chitosan NPs using the commonly used ionic gelation method. In one embodiment the process for preparing an extended release formulation for a water soluble pharmaceutical agent comprises four steps. The first step, the protonation of chitosan polymer amino groups, occurs in an acid environment (e.g. 2% v/v acetic acid aqueous solution, (J. Cho, et al., Biomacromolecules. 6:3267-3275 (2005)). This suggests that SAA salt aqueous solution which has a basic pH cannot not be used as an alternative solution to dissolve chitosan polymer. In the second step sodium hydroxide solution is added to raise the pH of the chitosan aqueous solution to 4.76 which is the pKa value of acetic acid. This addition of sodium hydroxide to raise of the pH of the protonated chitosan solution to 4.76, allows selective neutralization of one half of the acetic acid used to protonate the amino acid groups of the chitosan polymer and produces half acetate ion while concomitantly increasing the amount of sodium ion in the medium (P. Constable, The Veterinary clinics of North America Food animal practice. 30:295-316, v (2014); S. Magder et al., Annals of the American Thoracic Society. 12:111-117 (2015)). The pKa of the amino acid groups of chitosan is ~6.3 based on Henderson HasselBach equation. At pH=4.76, the amino groups of the chitosan polymer are still highly protonated. In the third step the pH of an aqueous solution of TPP in is lowered to the range of 5.5-5.99; it is believed that this avoids the competitive binding of between hydroxide ion ($OH^-$) formed instantaneously after dissolution of $Na_5TPP$ in deionized water (pH>9), and polyanion triphosphate (TPP) with the protonated amino acid groups of chitosan polymer during the formation of NPs by ionic gelation (F. MI, et al., Journal of Applied Polymer Sciences. 74:1093-1107 (1999)). Triphosphoric acid, the acid form of the polyanion TPP can undergo as many as 5 dissociations, therefore has 5 pKa values (pKa1=1; pKa=2.2; pKa3=2.3; pKa4=3.7 and pKa=8.5) (A. Holleman, et al., Inorganic Chemistry, Book, ISBN 0-12-352651-5:729 (2001)). That indicates that at pH=pKa4+2=5.7, TPP is almost fully ionized based on the Henderson Hasselbalch equation and may crosslink with protonated amino groups of chitosan polymer through electrostatic attraction. At this step of the process, the TPP aqueous solution or mixture with the drug (TFV) was added dropwise into protonated chitosan aqueous solution. The color of the solution changed from colorless to milky (Thyndall effect) indicating the formation of the NPs (W. Hu, et al., ACS applied materials & interfaces. 7:4728-4736 (2015)). As can be seen in Table 2, the EE % of TFV is low prior to the freeze drying step. In fact, the water soluble drug escapes the NPs compartment during the centrifugation favoring its concentration in the supernatant phase. This limitation of the drug encapsulation is overcome by avoiding the centrifugation step and by freezing at (−20° C.) or in liquid nitrogen (−194° C.), as described in the examples. The fourth step is the in situ coating of sodium acetate on the surface of chitosan NPs during the freeze drying process. Indeed, on the phase diagram temperature-composition, the eutectic point of the binary systems comprised of water and acetic acid, is reached at −26.7° C. with 59% w/w acetic acid (T. Padhiyar, et al., Internationnal Journal of Scientific Engineering and Technology. 2:211-215 (2013)). This suggests that at the used freeze drying operating condition of the above freeze dryer, (temperature −48° C., pressure ~0.06 mBar) and ~2.1% w/w acetic acid, any mixture of ice and acetic acid is solid (Padhiyar, 2013) and is co-sublimated during the lyophilization process. There is a highly uniform, and dense deposition of sodium acetate salt on the surface of the NPs. The in situ formation of sodium acetate may be due to the electrostatic attraction between the negatively charged acetate ion with the positively charged sodium cation generated mostly from sodium hydroxide (2M). In fact, this electrostatic attraction between acetate ion negative charge and positively sodium ion follows Debye-Hückel theory which states that, in a solution (e.g. before freezing the NPs suspension), near a given ion, counter ions are likely to be found and vice versa (P. Paula. Atkin's Physical Chemistry, ninth edition. Book, ISBN 978-0-19-954337-3:196 (2010)). Thus acetate ions and sodium ion are found close to each other around chitosan NPs in solution. Upon freeze drying, the sodium acetate salt is formed in situ through electrostatic attraction on the surface of chitosan NPs. We have a new coreshell sytem in which the core is TFV loaded chitosan NPs, and the shell is sodium acetate as shown in FIG. 2, panels D, E, and F. The corehsell NPs are very stable at room temperature. Unlike the zeta potential (ZP) of non-freeze dried chitosan NPs, the intermediate product, which was positive, as shown in Table 2, the ZP of coated/freeze dried NPs was consistent with that of the pure salt further confirming coating by sodium acetate.

Figure 5A:
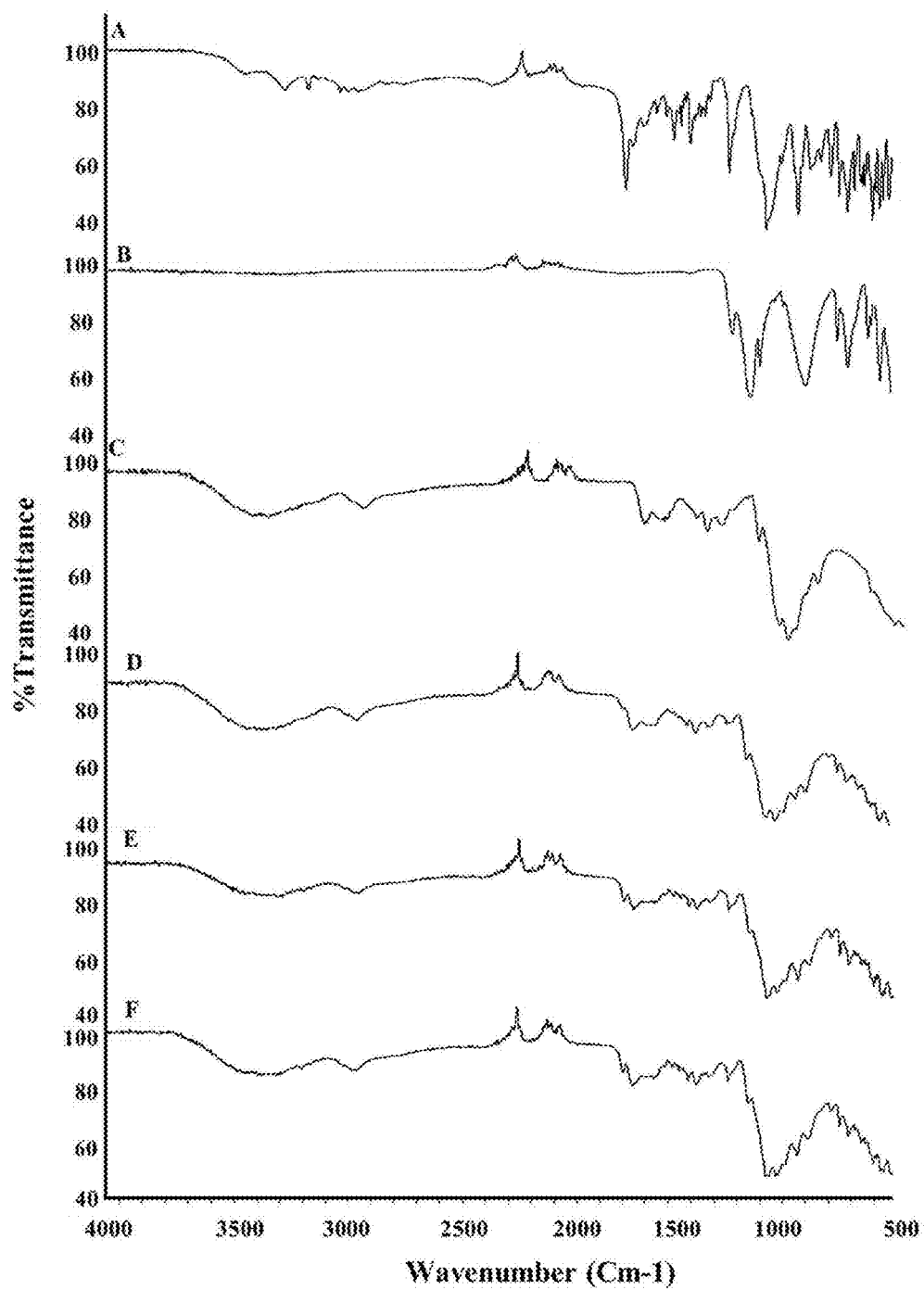
FIG. 5A. FTIR spectra of tenofovir (A), pentasodium phosphate (B), chitosan (C), physical mixture P1 (D), physical mixture P2 (E), and physical mixture P3 (F).
Figure 5B:
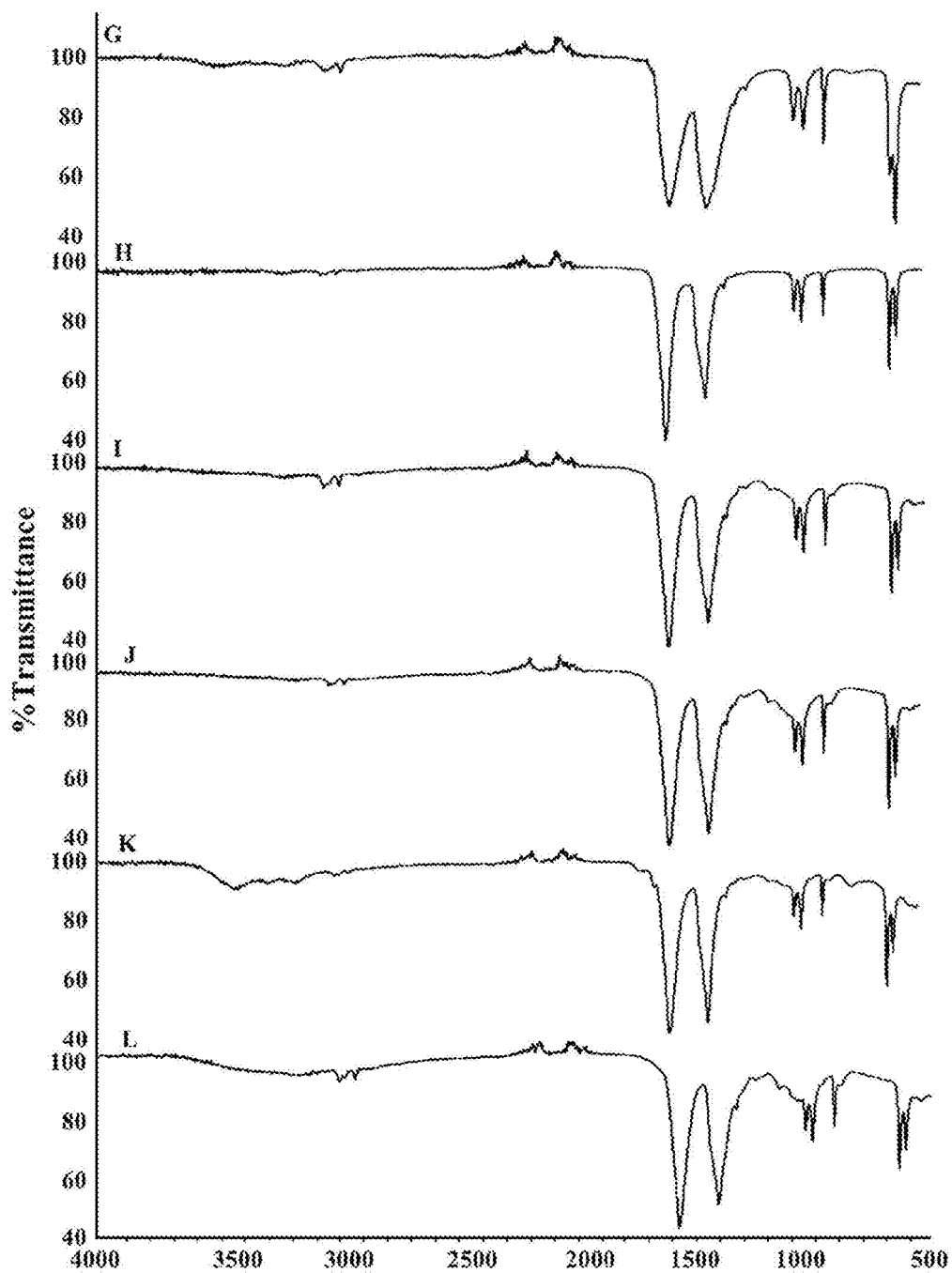
FIG. 5B FTIR spectra of sodium acetate anhydrous (SAA) (G), pure sodium acetate coating chitosan NPs (SA) (H), blank formulation (I), formulation F1 (J), formulation F2 (K), and formulation F3 (L).

The presence of the coating of salt on the surface of the NPs is also consistent with the FTIR analysis as shown in FIG. 5. Collectively, these results confirmed the presence of the salt coating on the NPs which were also consistent with the surface morphological analysis of the NPs as shown in FIG. 2 (see FIG. 2, panels D, E and F) showing a discrete, uniform, and unique coating layer of sodium acetate on the surface of chitosan NPs. The two bands (FIG. 5, panels G-L) in the FTIR spectrum at 1572.89 $cm^{-1}$ and 1411.55 $cm^{-1}$ are consistent with the presence of the carboxylate group of sodium acetate. (D. Mayo, et al., Wiley & Sons Publication: 210-213 (2004)). The antisymmetric stretch and symmetric stretch of single bond C—O is found at 1042.48 $cm^{-1}$ and 921.37 $cm^{-1}$ respectively (Mayo, 2004). The bands at 3000.04 $cm^{-1}$ and 2940.67 $cm^{-1}$ are consistent with the antisymmetric stretching vibration of $CH_3$, and overtone transition from the ground state to the second excited state of the $CH_3$ symmetric distortion respectively.

Figure 6A:
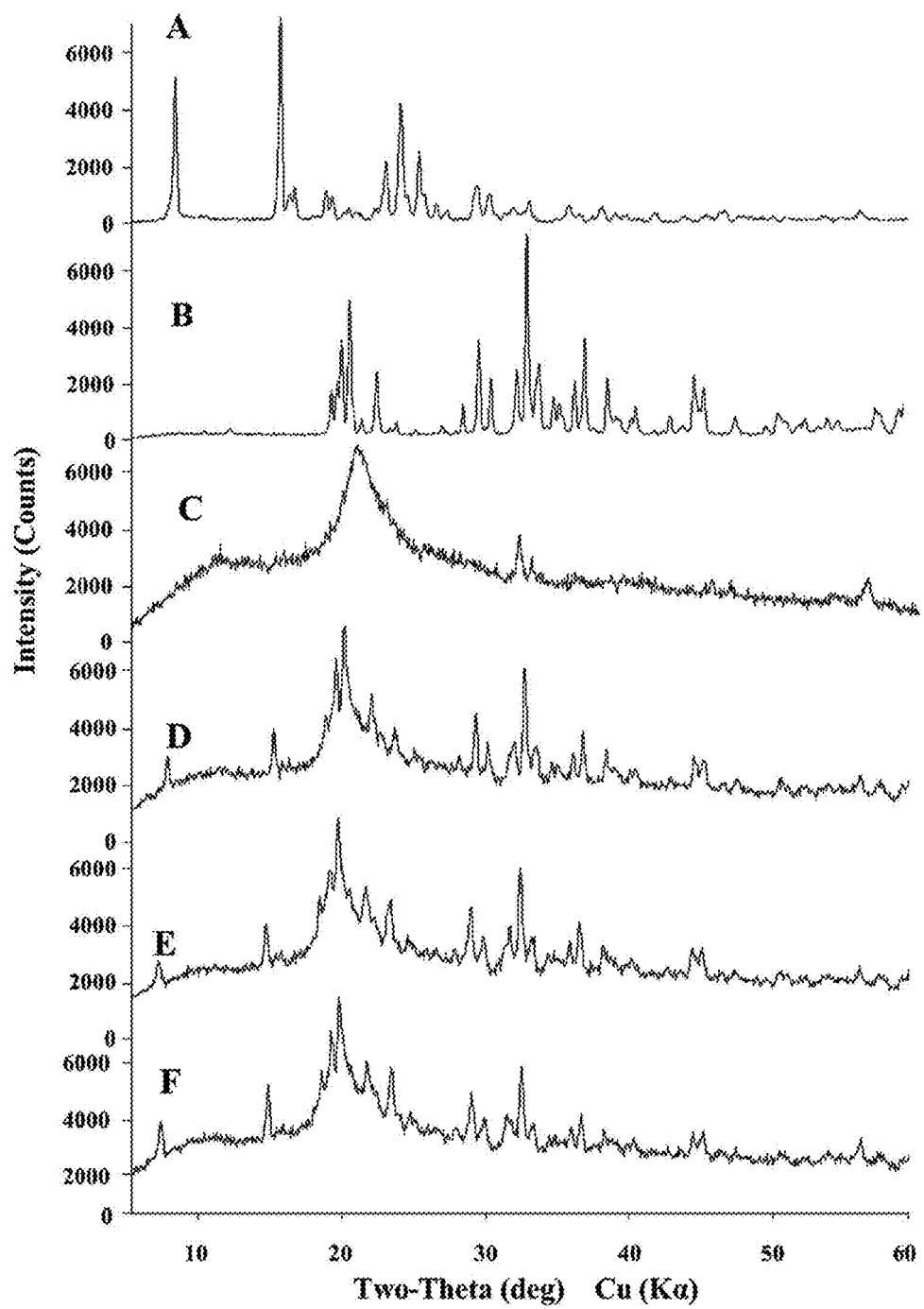
FIG. 6A. XRD pattern of tenofovir (A), pentasodium phosphate (B), chitosan (C), physical mixture P1 (D), physical mixture P2 (E), and physical mixture P3 (F).
Figure 6B:
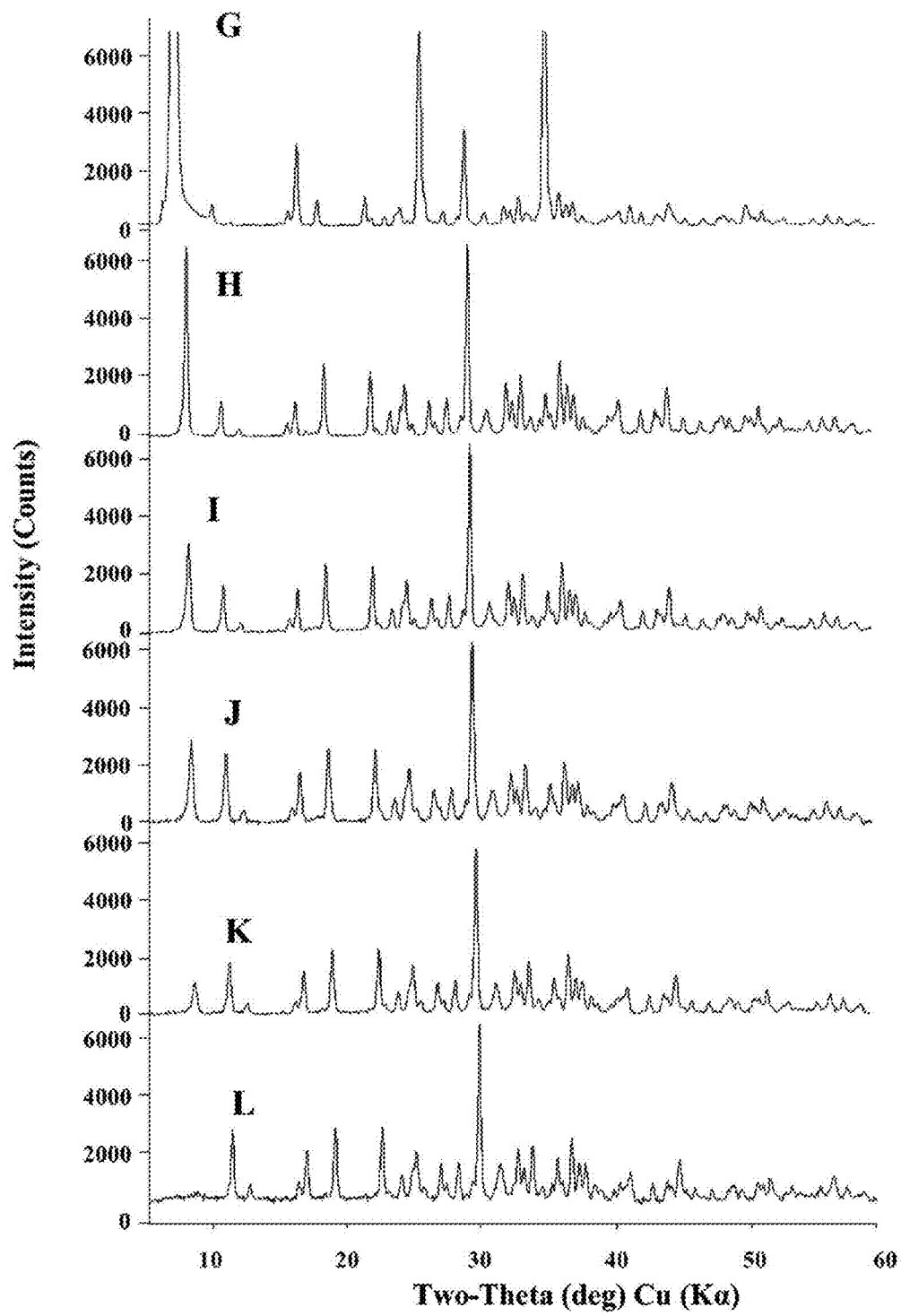
FIG. 6B. XRD pattern of sodium acetate anhydrous (SAA) (G), pure sodium acetate coating chitosan NPs (SA) (H), blank formulation (1), formulation F1 (J), formulation F2 (K), and formulation F3 (L).

There are different crystal structures for monobasic acetic acid salt. For instance sodium diacetate (SD) crystallizes in the cubic system (space group=Ia3) (M. Barrow, et al., Journal of Chemical Society Perkin 2:15-17), whereas sodium acetate trihydrate (SAT) crystallizes in the monoclinic system (space group=C2/C) (T. Cameron. Acta Crystallographica Section B. 32:87-90 (1976)). The physical mixtures (FIG. 6, panels D, E, and F) P1, P2, and P3 show peaks for the individual components, i.e. chitosan, TFV, and TPP, but not for sodium acetate. This is to be expected for a dry physical mixture of components. The "blank", and the three formulations (FIG. 6, panels I, J, K and L) show peaks for the pure salt (SA) (FIG. 6, panel H) coating the NPs. The angular positions of both SAA (FIG. 6, panel G) and SA (FIG. 6, panel H) of the diffracted beams which defined the shape and size of the unit cell were almost the same as shown in FIG. 6 (S. Stock. Elements X-Ray Diffraction Book, ISBN 0-201-61091-4. 3 296 (2001)). Thus SA and SAA are qualitatively identical as shown in FIG. 6. The XRD result appears to be consistent with the FTIR and the TEM results. Indicating the coating of the chitosan NPs with sodium acetate.

(SAA), (SAT), and SD, were used as controls to find the molar mass of the salt coating (SA) on the NPs surface using perchloric acid as a titrant. As shown in Table 3, the molar mass of the new salt is find to be 80.38±0.42 g/mol (n=3), after correction which nearly matches the molar mass of SAA (82.03 g/mol). This result is in agreement with the melting point data, used to assess the purity of the new salt. As shown in Table 3 the melting point of the new salt sodium acetate is 333-338° C. which was almost identical to the melting point of SAA 332.5-338° C.

Figure 3:
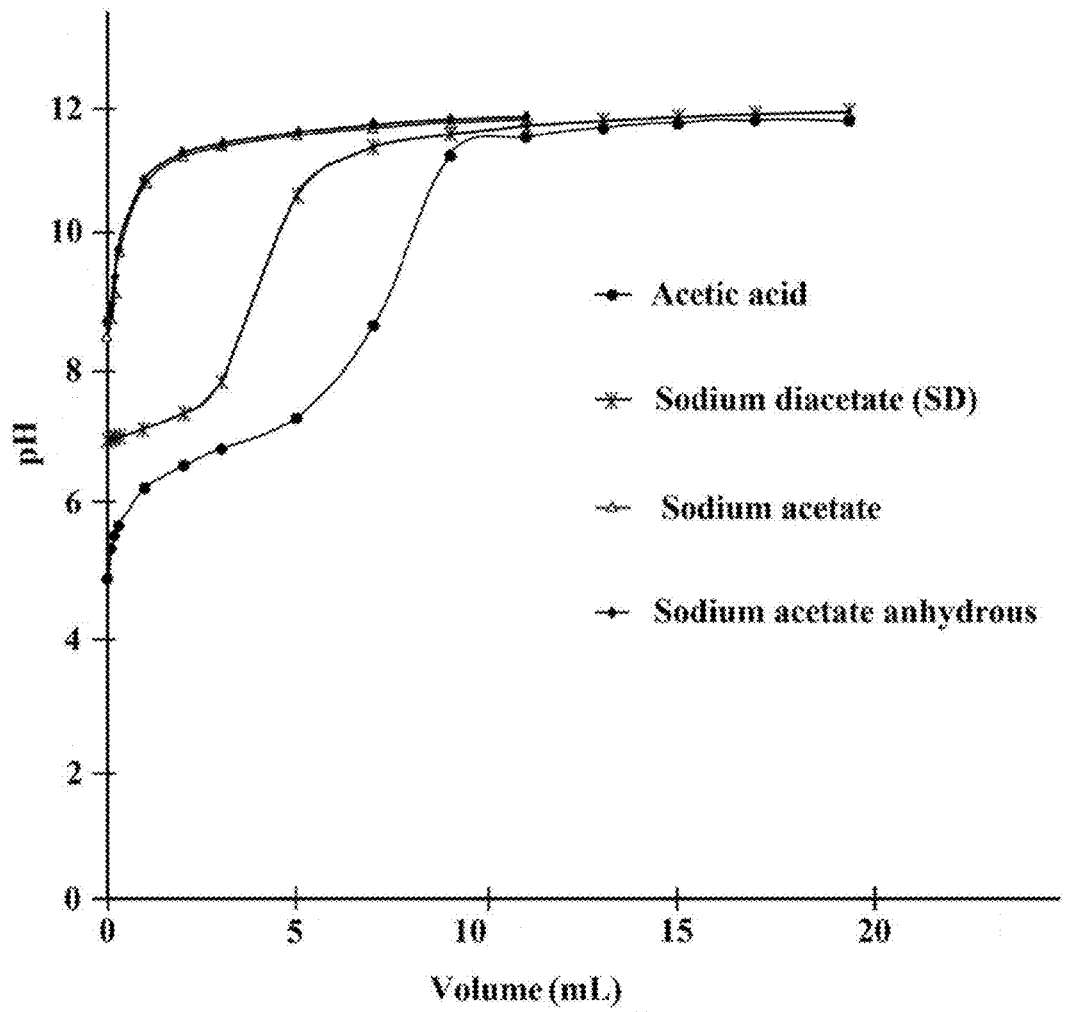
FIG. 3. Titration curve of different acetic acid salt with lithium methoxide in methanol (0.015M).

These above results are also consistent with the non-aqueous titration of the new salt with LM used a titrant. It clearly shows that the new salt formed is indeed sodium acetate. As shown in FIG. 3, the titration curve of both SAA and SA almost overlapped. This suggested that the salt coating chitosan NPs was indeed sodium acetate. This result was consistent with the above results. The titration curve which does not have an inflexion point, as shown in FIG. 3, suggesting that the salt did not contains acetic acid.

Collectively FTIR, XRD, melting point, and non-aqueous titration results indicate that, the shell coating chitosan NPs was indeed sodium acetate salt.

Figure 4:
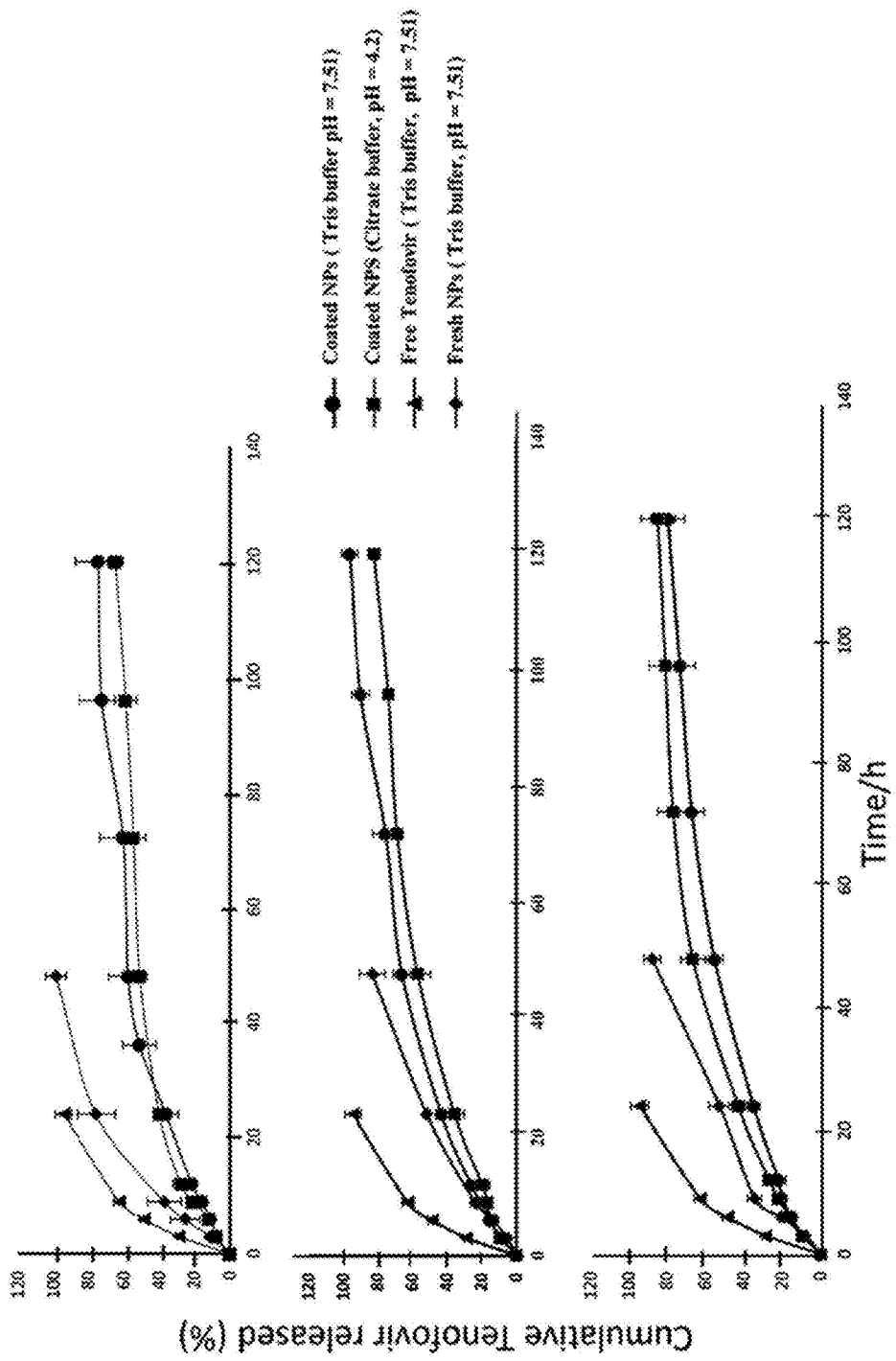
FIG. 4. In vitro release study A: formulation F1, B=formulation F2, and C=formulation F3. Release of coated NPs in tris-Hcl buffer pH=7.51 (dot marker), and in citrate buffer pH=4.2 (square marker) respectively. Release of TFV from fresh NPs (diamond marker) and release of free TFV (triangle marker), respectively.

The sodium acetate salt coating chitosan NPs exhibits several potential advantages. Firstly, it dramatically increases the EE % of TFV by 8-17 fold as shown in Table 2. Secondly, the coating prevents the aggregation of chitosan NPs as shown in FIG. 2, without the use of cryoprotectant with a slight increase of the size of the NPs due to the sodium acetate layer. The PDI of the NPs is conserved after freeze drying as shown in Table 2. Thirdly, the coating NPs exhibit sustained release of TFV as shown in FIG. 4 avoiding burst release compared to the control NPs. Based on the Korsmeyer-Peppa model, (P. Costa et al., (2001)) the release mechanism is an anomalous transport with 0.61<n<0.86, for the three different formulations (F1, F2 and F3) as shown in Table 5. It is believed that the release of TFV from the chitosan NPS (core) follows a combination of both a fickian-controlled drug release and a swelling-controlled drug release (M. Chavanpatil, et al., Int J Pharm. 316:86-92 (2006)) under continuous erosion of sodium acetate (shell structure). Unlike the stable core (chitosan NPs) with a ZP (24.3-28.5 mV), the erosion of the shell structure in aqueous solution, a key condition for drug release, is consistent with the ZP of pure sodium acetate as shown in Table 2, which is between 0-3 mV. However, this erosion is relatively slow and time dependent. As shown in FIG. 2, in panels E and F, sodium acetate layer is still visible after 24 hours of incubation in the release media at 37° C. It is appreciated that the thickness of the coating layer may be controlled by varying the initial concentration of the acetic acid and NaOH solutions. It is further appreciated that controlling the thickness of the sodium acetate shell may be used to yield controlled and sustained release of the bioactive agent in the biological matrix. It has been observed that it is very difficult to dissolve or suspend a portion of the non-coated chitosan-TPP "cake", in water (no apparent dissolution was observed), whereas, coated NPs can easily be re-suspended in water. It is appreciated that the core-shell NPs described herein may be used to improve the solubility and delivery of poorly water soluble drugs.

Figure 7:
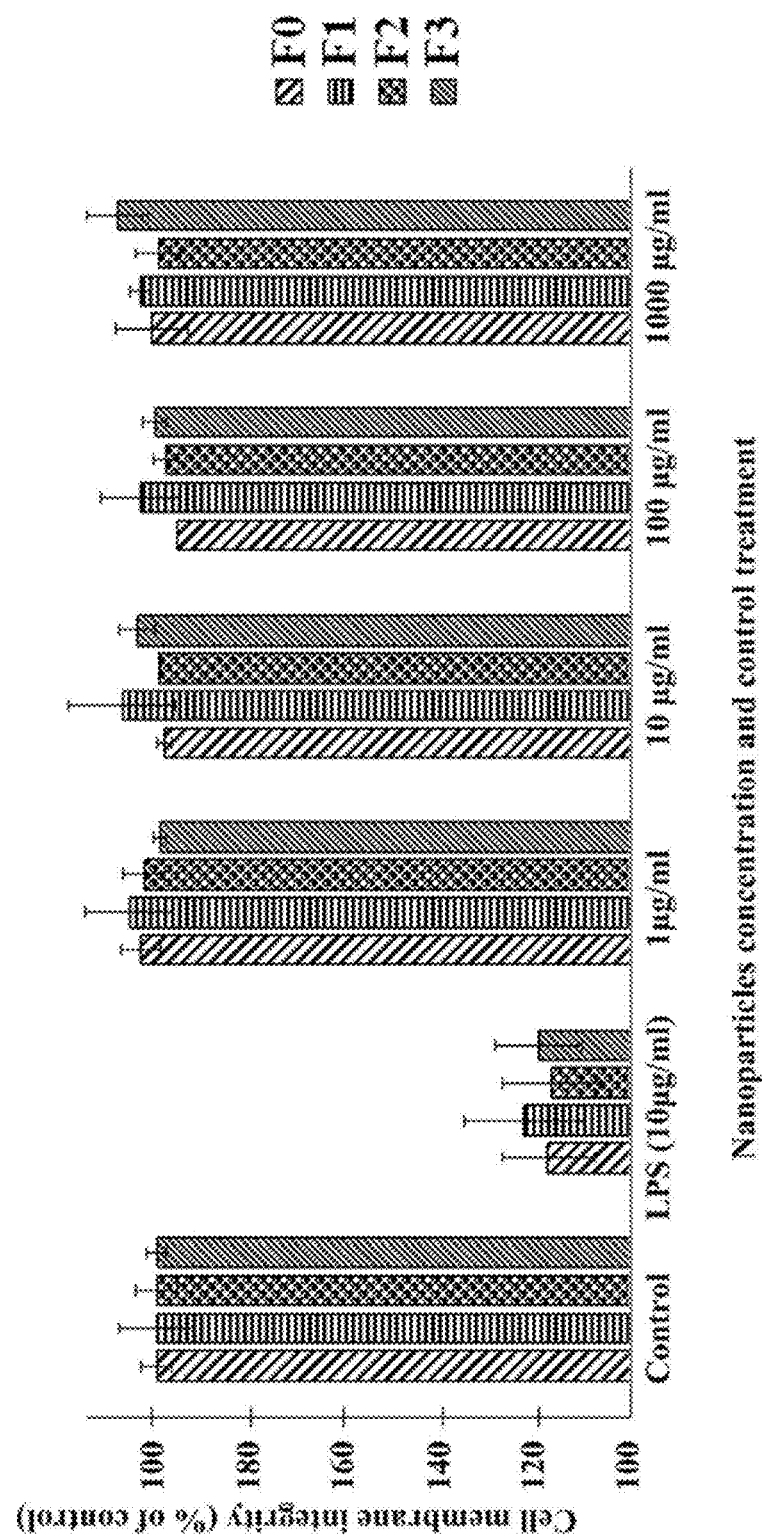
FIG. 7. Percent RAW 264.7 cell membrane integrity (% control) treated with the different NPs formulations F0 (pattern fill, downward diagonal), F1 (pattern fill, horizontal), F2 (pattern fill, sphere), and F3 (pattern fill, upward diagonal) respectively (n=3).*P<0.05 vs media, P<0.01 vs media, *P<0.001 vs media.

Based on International Organization for Standardization (ISO) ISO 10993-5 for cell viability, with 100% viability assigned to the control, cell viability higher than 80% is considered not cytotoxic; viability within 80%-60% is considered weakly cytotoxic; viability within 60%-40% is considered moderately cytotoxic and viability below 40% is considered strongly cytotoxicity (J. Lopez-Garcia et al., Journal of Functional Biomaterials. 5:4344). Sodium acetate coated chitosan NPs appear safe to the macrophage cell line as measured by several different criteria. Exposure to core shell NPs did not appear to damage the cell membrane. As shown in FIG. 7 there is higher accumulation of NR in lysosomes with a cell viability ~100%, suggesting that the NPs are safe to the macrophage cell. Exposure to NPs appears not to affect mitochondrial activity as shown in FIG.

Figure 9:
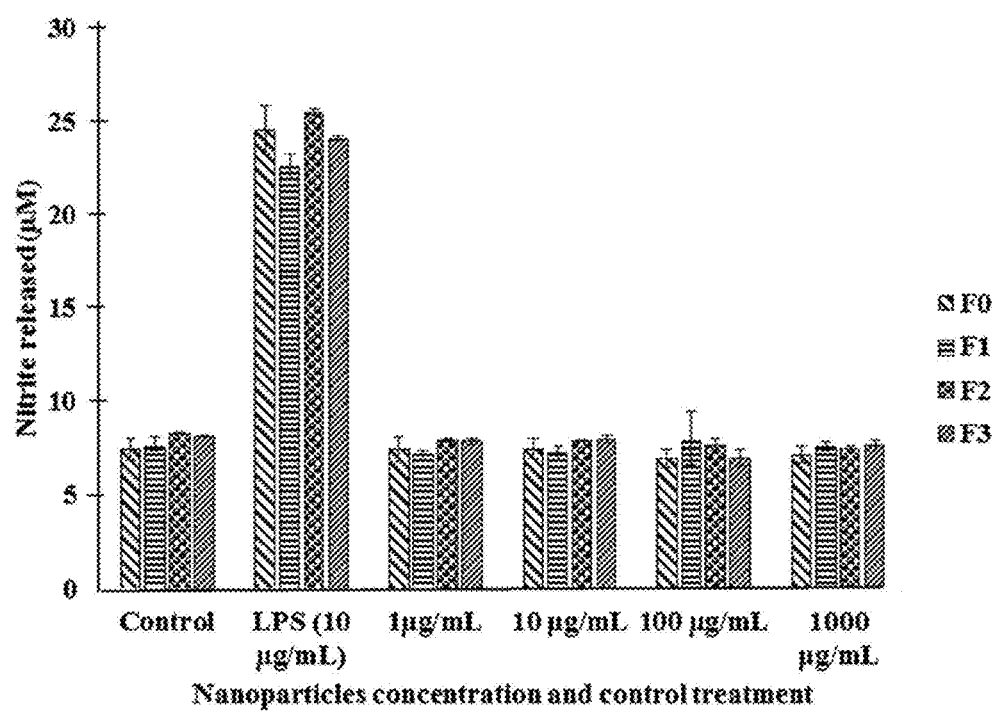
FIG. 9. Percent nitrite released from RAW 264.7 when exposed to the different NPs formulation FO (pattern fill, downward diagonal), F 1 (pattern fill, horizontal), F2 (pattern fill, sphere), and F3 (pattern fill, upward diagonal) respectively (n=3).
Figure 10A:
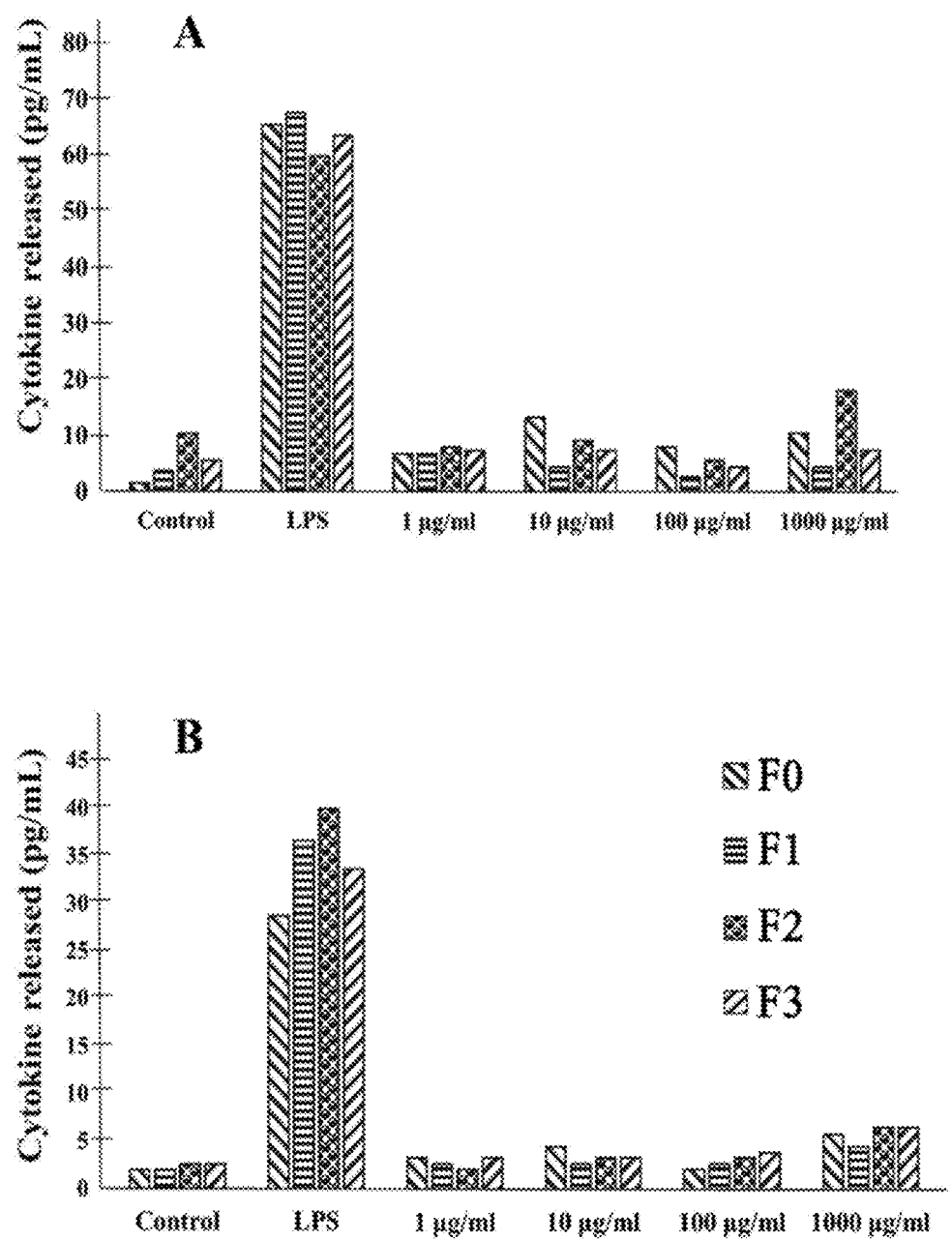
FIG. 10A. Percent cytokine/interleukin (IL) (A and B) respectively for IL$\alpha$ and IL$\beta$ release from macrophage when exposed to the different NPs formulation FO (pattern fill, downward diagonal), F1 (pattern fill, dark horizontal), F2 (pattern fill, sphere), and F3 (pattern fill, dark upward diagonal) respectively (n=2).
Figure 10B:
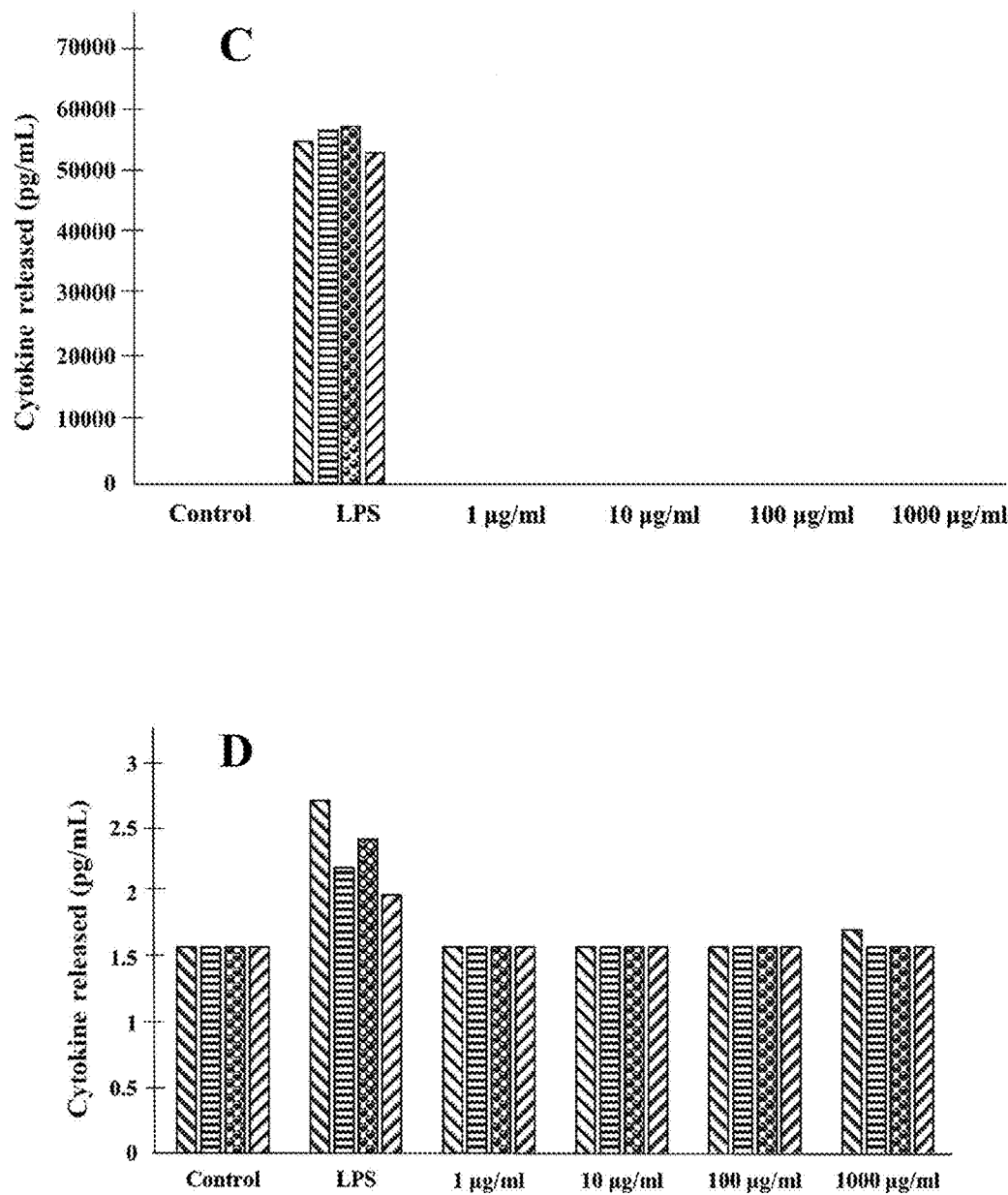
FIG. 10B. Percent cytokine/interleukin (IL) (C and D) respectively IL-6 and IL-7 release from macrophage when exposed to the different NPs formulation FO (pattern fill, downward diagonal), F1 (pattern fill, dark horizontal), F2 (pattern fill, sphere), and F3 (pattern fill, dark upward diagonal) respectively (n=2)

8 with a cell viability also ~100%. Exposure to NPs appears not to induce a pro-inflammatory response associated with macrophage activation based on the low level of NO production which is comparable to the base level as shown in FIG. 9. Exposure of RAW 264.7 to NPs resulted in low levels of IL-1α, IL-1β, IL-6 secretion into the supernatant. This appears to be consistent with other indicators that the core shell NPs did not induce a pro-inflammatory response associated with macrophage activation. (See FIG. 10. panels A, B, and C. In addition, the production of IL-7 matching the base level, appears to show that the NPs may not promote HIV infection as shown in FIG. 10, panel D (A. Introini, et al., PLoS pathogens. 9:e1003148 (2013)) and might be used a potential candidate for topical HIV microbicide carrier.

It is appreciated that sodium acetate coated NPs be used for (i) masking unwanted taste and for moisture protection of pharmaceutics (U. Stange et al., Pharmaceutical Development and Technology, 19.2 (2014): 137-147; S. Joshi et al., Int J Pharm. 457:395-406 (2013)44, 45), (ii) to prevent enzyme degradation (S. Gunawan, et al., Small. 10:4080-4086 (2014)), (iii) to increase the shelf-life of the pharmaceutical product (A. Elbarbary et al., Carbohydrate polymers. 104:109-117 (2014)) or used as a preservative. It has been discovered herein that sodium acetate (SA) can be used to coat chitosan NPs resulting in improved properties. The NPs described herein exhibited higher encapsulation efficiency (90%) of water soluble drugs such as tenofovir. It has been discovered herein that acetate salt coating of NPs reduce or eliminate aggregation of the NPs during the freeze drying process. NPs described herein or prepared by the processes described herein appear to be non-cytotoxic to a macrophage cell line while providing sustained release of tenofovir.

Representative biodegradable polymers useful in the processes described herein include, but are not limited to, poly(L-lactide) (PLLA), poly(D,L-lactide) (PDLLA), poly (lactic-co-glycolic acid) (PLGA), (poly)caprolactone (PCL), chitosan, and the like.

It is appreciated that drugs with low water solubility can be encapsulated in biodegradable polymers, using processes described herein or by processes well known to those skilled in the art of preparing polymeric formulations of bioactive materials.

As used herein a bioactive compound is a compound selected from the group consisting of flavoring agents, fragrances, herbicides, fungicides, rodenticides, nematacides, insect repellents, and pharmaceutical agents.

As used herein a pharmaceutical agent is any compound used to diagnose, cure, treat, or prevent disease. Some illustrative examples include, but are not limited to enzyme inhibitors, hormones; antibiotics; antiparasitics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and imaging compounds.

As used herein an aqueous dispersion is made up of fine particles of a bioactive material that are uniformly distributed throughout the aqueous portion of the dispersion Improved aqueous dispersion generally refers to improved uniformity of the dispersion, smaller particle size of the bioactive material in the dispersion, ease of forming the aqueous dispersion from a solid form of the bioactive material, and/or lower levels of aggregation of the fine particle during storage of the dispersion.

In any of the embodiments of the processes or formulations described herein the structure of the NP comprises a core particle of biodegradable polymer encapsulated with sodium acetate. In another embodiment, any of the embodiments described herein the NP has a sodium acetate shell with a thickness that is about 5% to about 7.5%, about 5% to about 10%, about 10% to about 15%, about 10% to about 20%, about 15% to about 25%, about 25% to about 50% or about 50% to about 100% of the diameter of the core.

EXAMPLES

The following abbreviations are used herein:
ANOVA analysis of variance
BCS biopharmaceutics classification system
DPBS Dubelcco's phosphate buffer saline
DMEM Dubelco's modified eagle medium
EE % encapsulation efficiency percent
F formulation
FBS fetal bovine serum
FTIR Fourier transform infrared
HSD honestly significant difference
IL Interleukin
LM lithium methoxide
LPS lipopolysaccharide
M molar mass
Mc molar mass corrected
NO nitric oxide
NPs nanoparticles
NR neutral red
PA perchloric acid
PDI polydispersity index
PMD particles mean diameters
SA sodium acetate,
SAA sodium acetate anhydrous
SAT sodium acetate trihydrate
SD sodium diacetate
TEM transmission electron microscopy
TFV tenofovir
TPP polyanion triphosphate
v Volume
XRD x-ray powder diffractometry
ζ zeta potential
Materials Chitosan, high molecular weight (% deacetylation degree of >0.75, viscosity=800 cps), sodium diacetate (SD), sodium acetate anhydrous (SAA), sodium acetate trihydrate (SAT), lithium methoxide (LM) in methanol (1M), methanol, acetonitrile, acetic anhydride, perchloric acid (PA), acetic anhydride were purchased from Sigma Aldrich (St. Louis, Mo., USA). Sodium triphosphate pentabasic ($Na_5TPP$), hydrochloridric acid, sodium hydroxide, and acetic acid glacial reagent were supplied by Fisher Scientific (Pittsburgh, Pa., USA). The murine macrophage RAW 264.7 (TIB-71) was purchased from the American Type Culture Collection (Manassas, Va., USA). Tenofovir (TFV) was purchased from Pichemicals (Zhang Jiang Hi Tech Park, Shangai, China). All other chemicals used in the study were of analytical grade and used as received without further purification.

Methods
Method of Preparation of Chitosan-TPP Nanoparticles

Chitosan-TPP NPs were prepared according to a modified ionic gelation method (7). Firstly, chitosan was dissolved in 2% V/V acetic acid glacial (pH~2.3) so that the final concentration of chitosan was 2 mg/mL over about 12-24 hours. Secondly, about 2.2 mL of sodium hydroxide (2M) was added to 20 mL of the aqueous chitosan solution to raise the pH of the solution from about 2.94 to 4.76 which is the pKa of acetic acid to produce enough acetate ion while keeping the pH of the solution acidic to keep the amino groups of chitosan protonated. Thirdly, 2 mg, 4 mg and 6 mg of TFV powder were added to 3 different beakers containing, TPP aqueous solution (V=4 mL, 2 mg/mL) respectively along with a blank formulation. The pH adjusted in the range (5.60-5.99) with a few drop of hydrochloric acid (2M) to minimize hydroxide ion amount in TPP aqueous solution respectively. Fourthly, the mixtures TPP-TFV aqueous solution (V=4 mL), with a total amount of TFV=2 mg, 4 mg, and 6 mg were added dropwise into three chitosan solutions (pH=4.76, V=20 mL) and named formulation F1, F2 and F2 respectively, along with a blank formulation as shown in Table 1. After 2-6 hours of continuous stirring, the colloidal solution was directly frozen at −20° C. for 18 to 24 hours or liquid nitrogen at −196° C. in few second and later on freeze dried with freeze dryer model 117 (A6532906) purchased from Labconco corporation (Kansas City, Mo., USA) without addition of cryoprotectants.

TABLE 1

|  | Physical mixture | | | | Formulation | | | |
|---|---|---|---|---|---|---|---|---|
|  | Blank | P1 | P2 | P3 | Blank | F1 | F2 | F3 |
| Chitosan amount (mg) | 40 | 40 | 40 | 40 | | | | |
| Sodium pentaphosphate amount (mg) | 8 | 8 | 8 | 8 | | | | |
| Tenofovir amount (mg) | 0 | 2 | 4 | 6 | | | | |
| Volume of chitosan aqueous solution in 2% v/v acetic acid (2 mg/mL, pH = 4.76)$^1$ (mL) | | | | | 20 | 20 | 20 | 20 |
| Volume of aqueous solution of triphosphate (2 mg/mL, pH = 5.60-5.99)$^2$ (mL) | | | | | 4 | 4 | 4 | 4 |
| Amount of tenofovir add into triphosphate aqueous solution (mg) | | | | | 0 | 2 | 4 | 6 |

$^1$pH raised with (2M, ~2.2 mL) of sodium hydroxide aqueous solution;
$^2$pH decreased with (2M, few drops) of hydrochloridric acid aqueous solution Sodium acetate (SA), the pure salt can also be prepared from 2% v/v aqueous solution of acetic acid glacial, after adjustment of the pH to 4.76 when the buffer solution is frozen gradually for 12 hours (−20° C.) or suddenly frozen with liquid nitrogen (−194° C.), respectively.

Aqueous solutions of chitosan, dissolved in 2% v/v glacial acetic acid are clear and colorless, formation of uncoated chitosan NPs through ionic gelation technique results in a milky appearing solution/suspension (Tyndall effect).

Uncoated chitosan NPs for the "blank", F1, F2, and F3 formulations using the classical ionic gelation use of a cryoprotectant results in aggregation of the NPs into a "cake" which is difficult to re-suspend in deionized water. Sodium acetate coated chitosan NPs do not exhibit this form of aggregation during freeze-drying resulting in a "cake" that is readily re-suspended in deionized water.

Particle Size Analysis

Fresh NPs were re-suspended by sonication (Qsonica LLC, Newtown, Conn., USA) in deionized water, or SA coated NPs were dissolved in deionized water and the particle size, the zeta potential, and polydispersity index (PDI) was measured through dynamic light scattering (Zetasizer Nano ZS, Malvern Instruments Ltd, Worcestershire, UK) at 25° C. Samples with polydispersity index (PDI) <0.05 were considered monodispersed according to the National Institute guidelines (7).

Encapsulation Efficiency (EE %) Determinations
Indirect Method for EE % Determination The amount of the TFV entrapped into the fresh NPs before freeze drying was calculated from the difference between the total amount of TFV initially used and the amount of drug found in the supernatant after encapsulation process. The free drug amount in the supernatant was measured using UV spectrophotometer (Spectronic Genesys 10 Bio, Thermo Electron Corporation, WI, USA) at a wavelength of 260 nm The drug EE % was calculated as follow:

$$EE\ \% = \frac{\text{Total amount of } TFV - \text{free } TFV}{\text{Total amount of } TVF} * 100 \quad (1)$$

The standard curve of TFV absorbance (Y), used is: Y=0.0448X ($R^2$=0.9994), where X=concentration of TFV (μg/mL).

Direct Method for EE % Determination

The amount of tenofovir entrapped in the NPs after freeze drying, was measured at 260 nm using the above UV spectrophotometer. Briefly, 1 mg/mL of different formulations (F1, F2, and F3), along with the appropriate blank were dissolved in 2M HCl up to 23 hours at room temperature and followed by 1 hour of sonication using the sonicator (Qsonica LLC, Newtown, Conn., USA). Then, the completely dissolved nanoparticles solutions was centrifuged (14,000 rpm, 10° C.) for 20 min using refrigerated microcentrifuge (VWR, Radnor, Pa.). Finally, the total amount of TFV entrapped, was recorded at 260 nm along with the appropriate blank, used to setup the baseline. The drug EE % % was calculated as follow $$:EE\ \% = \frac{\text{Total amount of } TFV \text{ entrapped}}{\text{Total amount of } TVF} * 100 \quad (2)$$

The same standard curve of TFV (equation 1) was used to assess the total amount of drug in the NPs because, the media does not appear to shift the calibration curve based on preliminary screening.

Fourier Transform Infrared (FTIR) Spectroscopy

The FTIR was used to confirm the chemical nature of the salt coating of the NPs after freeze drying. The spectra were recorded on a Nicolet 860 FTIR Thermo Electron (Nicolet iS10 FT-IR Spectrometer with OMNIC Spectra software, Thermo Scientific, West Palm Beach, Fla.) at a range of 600-4000 $cm^{-1}$, and 2 $cm^{-1}$ resolution. Powdered samples, of the, blank NPs or TFV loaded NPs, were deposited on the crystal for analysis at room temperature.

X-Ray Powder Diffractometry (XRD)

XRD was used to study the crystallinity of the NPs coated with SA. The powder XRD scans were performed using a MiniFlex automated X-ray diffractometer (Rigaku, The Woodlands, Tex.) at room temperature. Ni-filtered Cu Kα radiation was used at 30 kV and 15 mA. The diffraction angle was covered from 2θ=5° to 2θ=60° with a step size of 0.05°/step, and a count time of 2.5 s/step (effectively 1.1°/min for approximately 46 minutes/scan). The diffraction patterns were processed using Jade 8+ software (Materials Data, Inc., Livermore, Calif.). The relatives intensities of the diffracted beams which were directed by the position of atoms can estimated using the following equations (S. Stock, Elements X-ray Diffraction, ISBN 0-12-352651-5:309 (2001));

$$I = |F|^2 \, p\left(\frac{1+\cos^2 2\theta}{\sin^2 \theta \cos \theta}\right) \quad (3)$$

$$F = \sum_i^N f_n e^{2\pi i(hu_n + kv_n + lw_n)} \quad (4)$$

Where, I=relative intensities of the diffracted beams, F=Structure factor for hkl in terms of atom position u v w, θ=Bragg angle, and p=multiplicity factor.

Non Aqueous Titration of Acetate Ion in the Salt with Perchloric Acid (PA)

PA solution (0.015 M) in acetic acid glacial, used as a titrant, was used also to determine the molar mass of the salt coating chitosan NPs. Three different samples, sodium acetate anhydrous (SAA), sodium acetate trihydrate (SAT) and sodium diacetate (SD) with a known molar mass were used as a control to confirm the molar mass. Crystal violet (dye) (0.0005% w/v, 100 μL) was used to determine the equivalence point. Briefly, approximately 10 mg of the appropriate salt was dissolved in 20 mL of acetonitrile, followed by addition of 100 μL of the dye, under continuous stirring. Then the amount of the acetate in salt was titrated with PA until the color of the solution changed from purple to green (J. Fritz, Analytical Chemistry. 22:(1950)). The molar mass of the salt is calculated using the following equation assuming the purity of the salt was ~100%:

$$M = \frac{m}{C_a V_a} \quad (5)$$

Where, M is the molar mass found of the salt, m=mass (g) of the salt, Ca=concentration of perchloric acid (0.015M), and V=Volume of PA added (L).

The molar mass M was corrected and term molar mass corrected ($M_c$) to find the true molar mass of the different salt using a reference the molar mass of SAA. The following equation allows us to find $M_c$ $$M_c = M * \frac{\text{expected molar mass of } SAA}{\text{average molar mass found of } SAA} \quad (6)$$

Non Aqueous Titration of Acetic Acid Content in the Salt with Lithium Methoxide (LM) in Methanol LM solution (0.015 M) in methanol, used as a titrant, was used to titrate the acetic acid content if any of the new salt dissolved in methanol (G. Harlow, et al., Analytical Chemistry. 30:(1958)). Glacial acetic acid glacial in methanol (0.006 M, 20 mL), SA~10 mg, SD~10 mg, dissolved in methanol were used as a control. Briefly, the appropriate salt (~10 mg, 20 mL) or 20 mL of the acetic acid glacial solution was titrated with LM using a pH-meter. The titration curve, pH=f (Vb) of the change of pH, due to the addition of the LM was plotted against the volume Vb; (Vb=volume of LM added). Microsoft Excel 2013 was used to fit the non-aqueous titration.

Method of Determination of Melting Point (MP)

The melting point of salt was measured to determine its purity. Briefly the salt was packed into a Kimble Chase capillary melting point tube made of borosilicate glass, 1.5-1.8×90 mm, purchased from (Fisher Scientific, USA). The tube was gradually heated in a MEL-TEMP capillary melting point apparatus (Sigma Aldrich, USA) and the temperature was measured with a Fluke 51 II digital thermometer containing a thermocouple probe (Fluke, USA) as a range from the appearance of the first drop of liquid to a complete melt of the salt.

Transmission Electronic Microscopy Analysis

The surface topography of the NPs coated with SA was visualized with the transmission electron microscopy (TEM). To get the specimens, the drops of NPs suspension were placed on a copper grid with a carbon support film and air dried. The NPs were viewed under a Scanning Transmission Electron Microscope CM12 (FEI, Hillsboro, Oreg., USA) at 80 kV accelerating voltage. Digital images were acquired with an ORIUS™ SC 1000 11 Megapixel CCD camera (Gatan, Pleasanton, Calif., USA).

In Vitro Drug Release Study

Twenty five milligrams, 12.5 mg and 8.33 mg of TFV respectively for the formulation F1, F2 and F3 containing approximately a total amount ~110 μg were dissolved in 4 mL of Tris-Hcl buffer (9.1 mM, pH=7.51) or citrate buffer (1M, pH=4.2) and put into a Spectra/Por cellulose ester membrane dialysis bag (Spectra/Por Float-A-LyzerG2, MWCO 3.5-5 KD, Spectrum Laboratories Inc. Rancho Dominguze, Calif., USA). The dialysis bag was then dipped into a tube of 50 mL total capacity containing 24 ml of the appropriate buffer. The whole system was incubated in a thermostatically controlled shaking (50 rpm) water bath (BS-06, Lab Companion, Seoul, Korea) at 37° C. At set time intervals, 1 mL of the buffer solution outside the dialysis bag was removed and replaced by fresh buffer solution to maintain a sink condition. The concentration of the drug released from the NPs in the outer tube solution was determined by a UV spectrophotometer at 260 nm as indicate in the EE % determination section. Each experiment was run in triplicate. In addition, the release curve was fitted with Korsmeyer-peppa model (P. Costa et al., Eur J Pharm Sci. 13:123-133 (2001)) to understand the release mechanism of TFV from the NPs, using the following equation;

$$\frac{M_t}{M_\infty} = at^n \quad (7)$$

Where, $$\frac{M_t}{M_\infty}$$

represent the fractional drug release, a is a constant combining structural and geometric features of the drug dosage form, and n typify the release mechanism (e.g. Fickian diffusion (n=0.5); anomalous diffusion (0.5<n<; case II transport (n=1) and super case II transport (n>1).

Macrophage RAW 264.7 Culture

Cells were grown and maintained in a monolayer culture, in 75 cm$^2$ culture flasks (TPP, Switzerland), at 37° C. in a humidified atmosphere of 5% carbon dioxide ($CO_2$) and 95% air.

Exposure Protocol

The NPs were freshly suspended in DMEM/FBS 5% at 1000 μg/mL, dispersed by sonication (VWR, model 150 D; VWR International, West Chester, Pa., USA) for 10 minutes, sterilized for 30 minutes under UV light (A. Wadajkar, et al., Adv Healthc Mater. 1:450-456 (2012)), and diluted 1:1, 1:10, 1:100 and 1:1000. Macrophages RAW 264.7 (2×10$^5$ cells/100 μL/well) were seeded in 96-well culture plates (growth surface: 0.34 cm$^2$) and incubated for 48 hours. Then, the cells were subjected for 24 hours to the NPs at 1, 10, 100 and 1000 μg/mL corresponding to 0.3, 3, 30 and 300 μg/cm$^2$, respectively. Wells containing cells without NPs were used as the negative controls. As a positive control, the macrophages were treated with LPS (10 μg/mL), a well-known activator to stimulate an inflammation (S. Panda, et al., PLoS Pathog. 8:e1002717 (2012)).

Assessment of Cell Membrane Integrity

The cell membrane integrity was measured using the specific accumulation of the vital dye neutral red (NR) in lysosomes (S. Lanone, et al., Part Fibre Toxicol. 6:14 (2009); E. Borenfreund et al., Toxicol Lett. 24:119-124 (1985)). After exposure to the NPs, the cells were washed twice with Dubelcco's phosphate buffer saline (DPBS), and then 100 μL of fresh medium containing 50 μg/mL NR (Sigma-Aldrich, St. Louis, Mo., USA) was added to each well and incubated for 3 hours. Then, the cells were washed twice with DPBS, and the dye was extracted with 1% acetic acid/50% ethanol (v/v). The plate was shaken for 15 minutes in the dark to solubilize all the NR crystals prior to the fluorescence intensity measurement (530-560 nm excitation, 590 nm emission) using a DTX 800 multimode microplate reader (Beckman Coulter, Brea, Calif., USA).

Assessment of Mitochondrial Activity

The mitochondrial activity was examined using a resazurin assay (Sigma-Aldrich, St. Louis, Mo., USA) (E. Vega-Avila et al., Proc West Pharmacol Soc. 54:10-14 (2011)). After exposure to the NPs, the cells were washed twice with DPBS, fresh medium was added, and then 10 μL of resazurin (0.1 mg/mL in DPBS) was added to each well. The assay plate was shaken for 30-60 seconds and incubated for 3 hours. Afterwards, the plate was shaken for 30-60 seconds prior to determining the fluorescence intensity (530-560 nm excitation, 590 nm emission) using the above microplate reader.

Assessment of Intracellular Nitrogen Species: Nitric Oxide (NO)

NO production in culture supernatant, a measure of inducible NO Synthase (iNOS) activity, was examined via nitrite accumulation measurement, the stable end product of the autoxidation of NO in aqueous solution (L. Connelly et al., J Immunol. 166:3873-3881 (2001); I. Kim et al., Toxicol In Vitro. 23:1014-1019 (2009)). After the indicated exposure period to the NPs, cell supernatants were collected and centrifuged at 1,000×g for 10 minutes to remove cellular debris and particulate materials. Then, 50 μL of the supernatant was placed into a new plate and mixed with the Griess reagents according to the manufacturer's instructions (Promega, Madison, Wis., USA). Absorbance was measured at 540 nm using the microplate reader and nitrite concentration was calculated using the sodium nitrite standard curve.

Assessment of Inflammatory Response and Promotion of HIV Transmission

Interleukin 1 alpha (IL-1α), interleukin 1 beta (IL-1β) and interleukin 6 (IL-6) production in culture supernatant, is a measure of inflammatory response stimulated by the exposure of the cell to the NPs. In addition, Interleukin (IL-7) production was also assess to elucidate if the NPs whether or not stimulate HIV transmission through a significant release of IL-7 (A. Introini, et al., (2013)). Quantitative measurements of both IL-1α, IL-1β and IL-6 released in the supernatant were measured through multiplexing with the use of magnetic bead kits (EMD Millipore, Billerica, Mass., USA) according to kit directions and analyzed on a MAG-PIX (Luminex, Austin, Tex., USA).

Statistical Analysis

All values were expressed as mean±standard deviations. One way analysis of variance with (ANOVA) in combination with all pairs Tukey's HSD (Honestly Significant Difference) post-test were used to find means of data that were significantly different from each other. All statistical analysis was carried out using JMP software version 10, (SAS Institute, Cary, N.C., USA). A P-value below 0.05 was considered statistically significant and allows the rejection of the null hypothesis.

Nanoformulation Physico-Chemical Properties

Particles Size Analysis

Figure 1B:
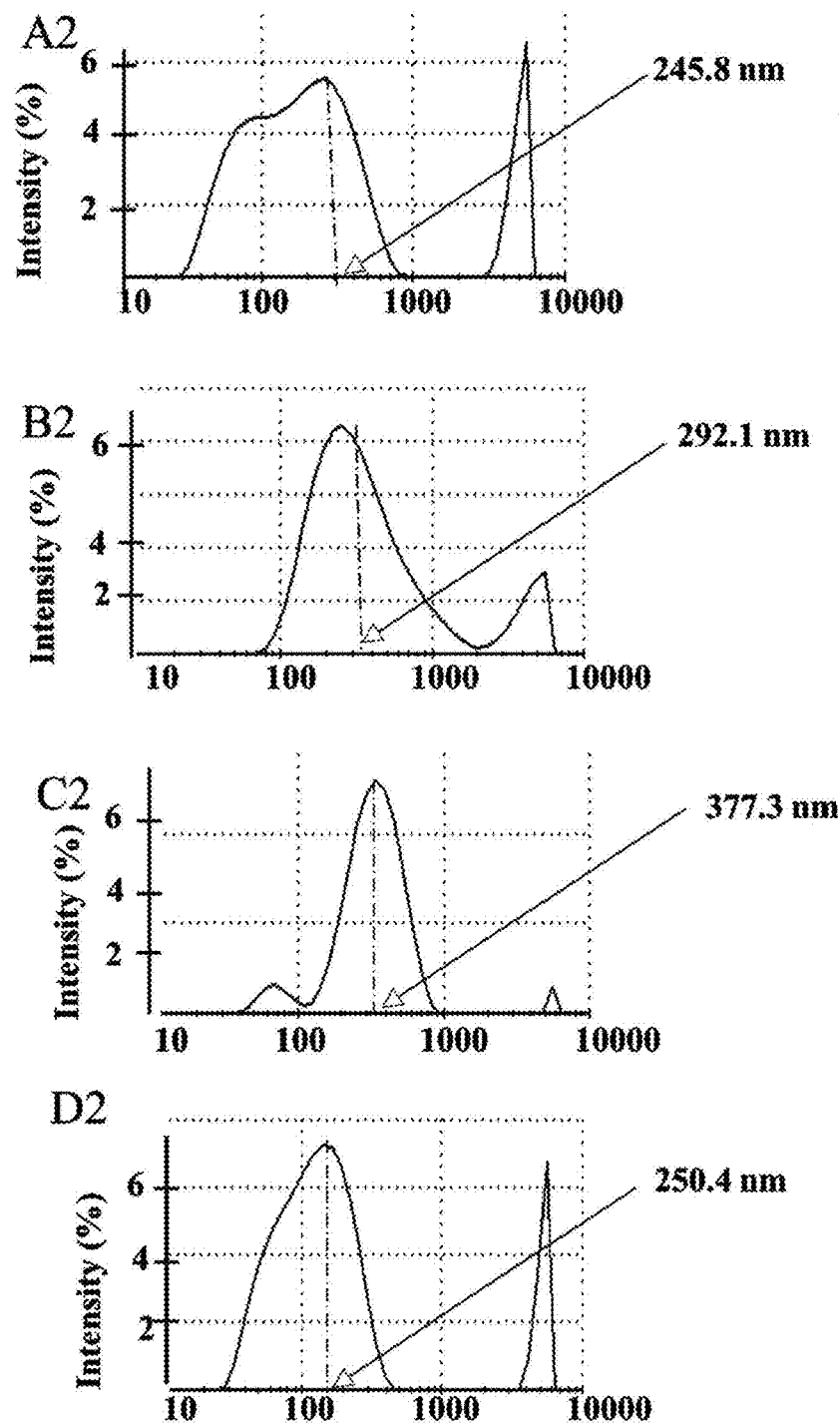
FIG. 1B. Particle size distributions by dynamic light scattering of chitosan coated with sodium acetate (A2, B2, C2, and D2) respectively for blank formulation, F1, F2 and F3 formulation respectively.
Figure 2A:
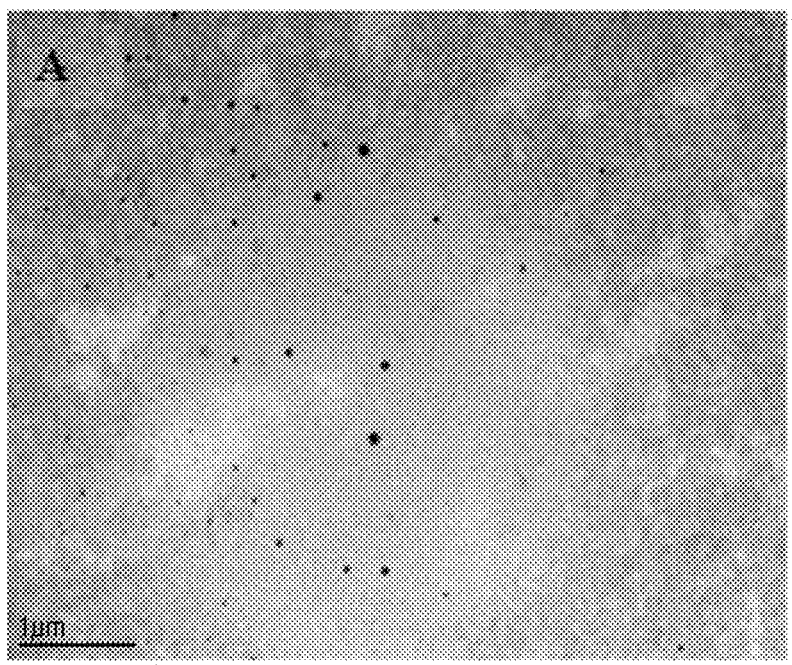
FIG. 2A. Transmission electron microscopy (TEM) of chitosan NPs (A, B) for the blank formulation before freeze drying Scale bar represents 100 nm for (B, D, E, F) and 1000 nm for (A, C) in FIGS. 2A, 2B, and 2C.
Figure 2A:
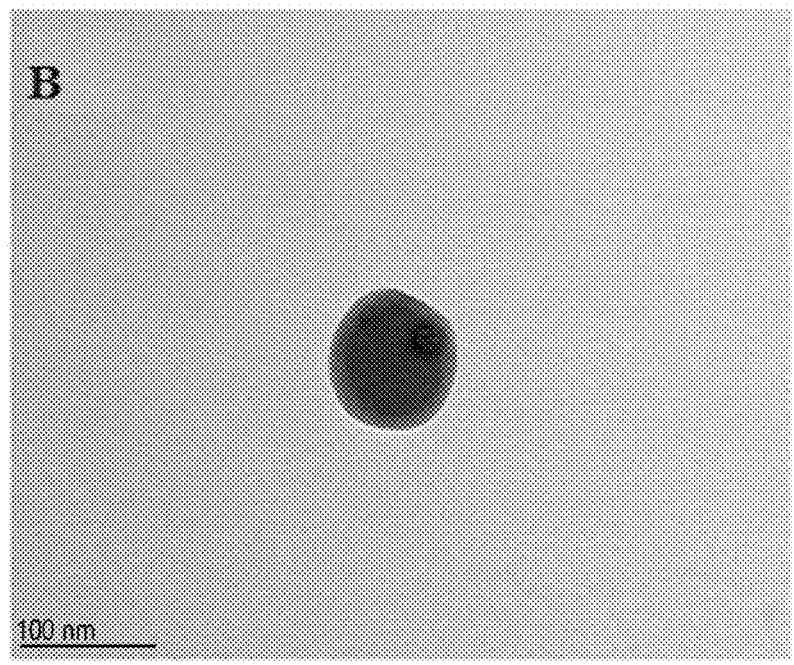
Figure 2B:
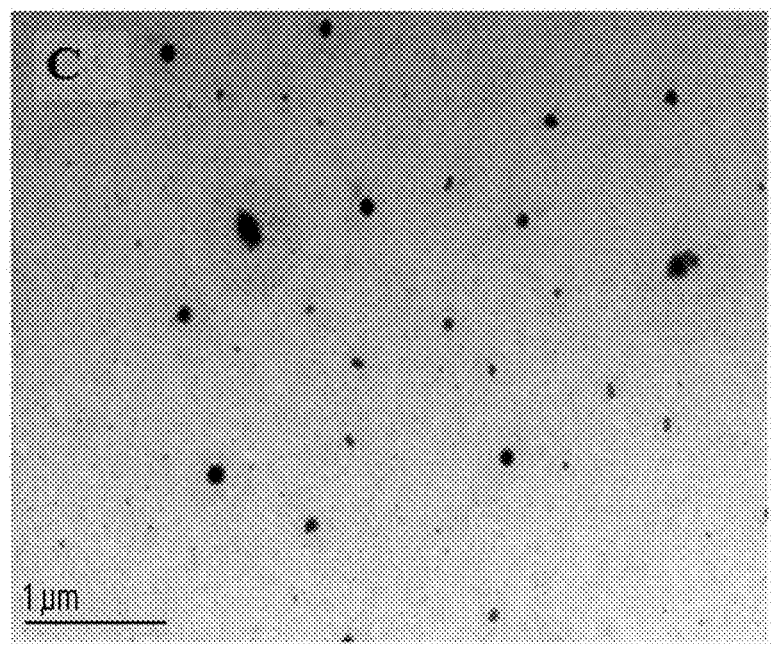
FIG. 2B. TEM of chitosan NPs (C, D) for the blank formulation after freeze drying.
Figure 2B:
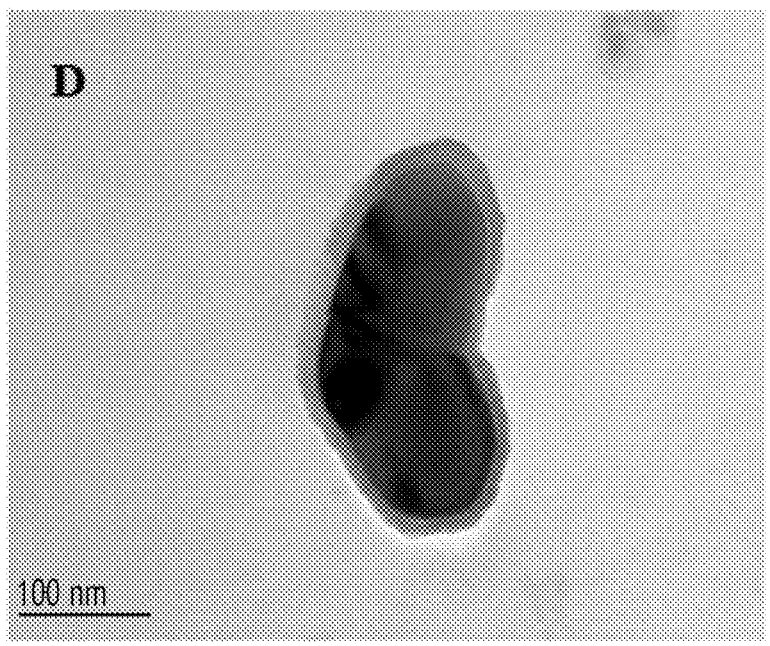
Figure 2C:
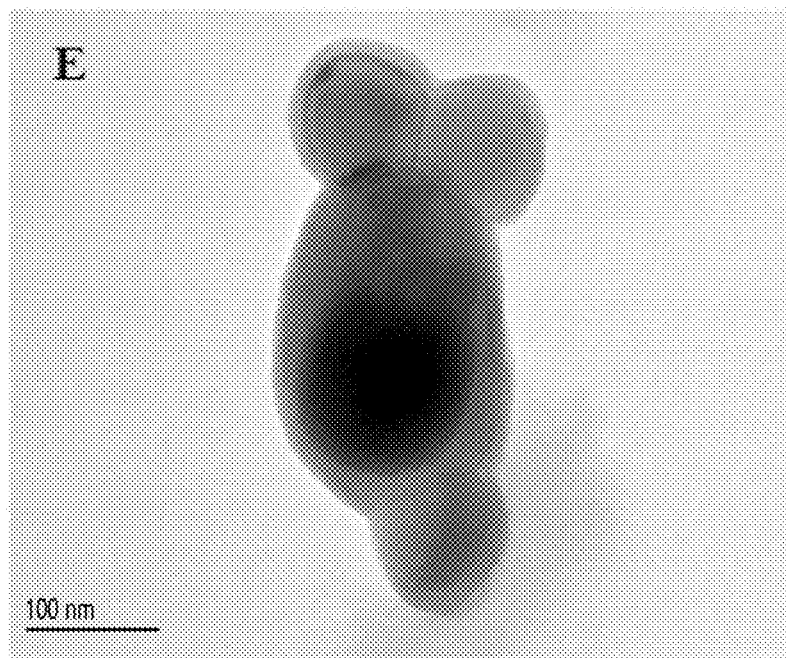
FIG. 2C. TEM of chitosan NPS (E, F) (blank) coated with sodium acetate after 24 hours, and incubated at 37° C. in tris HCl buffer pH 7.51.
Figure 2C:
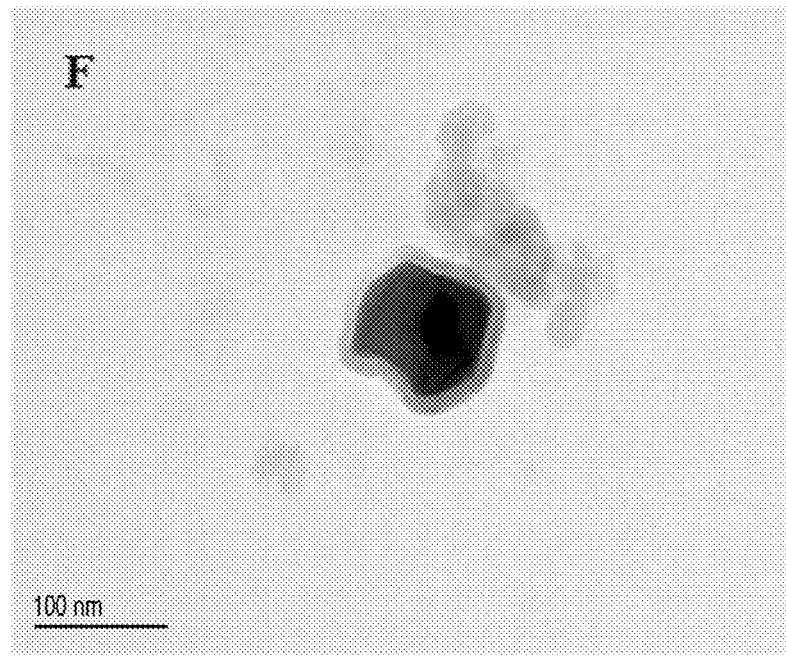

The particles size for the blank and the three different formulations before and after freeze drying, (F1, F2 and F3) as well as the zeta potential and PDI are shown in Table 2. The PDI of the NPs is conserved before and after freeze drying (Table 2) suggesting that the coating salt prevent aggregation of the NPs. However, size increases slightly due to the additional thickness of the shell, (SA) on the core chitosan NPs as shown in Table 2. FIG. 1 shows, respectively, the size of fresh NPs size before (A1, B1, C1, and D1) after freeze-drying (A2, B2, C2 and D2). The summary of the particle size as well as the encapsulation of all the formulations is shown in Table 2.

TABLE 2

Particle sizes, zeta potential, polydispersity index, and encapsulatuion efficiency for different formulations (F)

| | Formulation | | | |
| --- | --- | --- | --- | --- |
| | Blank | F1 | F2 | F3 |
| Size NPs before freeze drying d. (nm) | 348.33 ± 74.64 | 135.67 ± 1.86 | 150.67 ± 1.2 | 155.93 ± 4.34 |
| Size NPS after freeze drying d. (nm) | 165.2 ± 70.01 | 261.23 ± 118 | 379.53 ± 130.26 | 171.53 ± 70.01 |

TABLE 2-continued

Particle sizes, zeta potential, polydispersity index, and encapsulatuion efficiency for different formulations (F)

| | Formulation | | | |
|---|---|---|---|---|
| | Blank | F1 | F2 | F3 |
| EE % before freeze drying | n/a | 11.74 ± 0.71 | 5.52 ± 0.34 | 6.12 ± 0.1 |
| EE % after freeze drying | n/a | 89.27 ± 0.77 | 92.74 ± 4.00 | 86.34 ± 4.53 |
| Zeta potential before freeze drying (ev) | 28.47 ± 2.07 | 25.97 ± 1.07 | 27.53 ± 2.05 | 24.3 ± 2.05 |
| Zeta potential after freeze drying) (ev) | 3.06 ± 1.95 | 0.08 ± 0.86 | 2.23 ± 0.68 | 1.22 ± 0.88 |
| PDI before freeze drying | 0.47 ± 0.05 | 0.30 ± 0.05 | 0.34 ± 0.07 | 0.32 ± 0.04 |
| PDI afer freeze drying | 0.30 ± 0.05 | 0.24 ± 0.02 | 0.37 ± 0.14 | 0.43 ± 0.08 |
| Zeta potential of pure salt (ev) | −4.87 ± 0.64 | | | |

Encapsulation Efficiency Determination

The EE % of TFV for the different formulations before and after freeze drying for are shown in Table 2. The EE % before freeze drying are indeed very low (EE %=5-11%) whereas those after freeze drying using the new process developped in this study are indeed high (EE % ~90%) and increases by ~8-17 fold as shown in Table 2.

Electron Micrograph

FIG. 2 shows the visualization of the NPs (A, B) and (C, D) before and after freeze drying respectively. The salt coating the NPs (C, E, and F) is visible after freeze drying. The coating of SA onto chitosan NPs gives a coreshell structure in which the shell is SA and the core is chitosan NPs.

Determination of the Melting Point (MP)

The MP of the different salts of acetic acid are shown in Table 3. The melting point of SA (salt prepared using the process described herein) is matches the melting point of SAA (commercial sample).

TABLE 3

Melting point of the different salt and molar mass of the different salt of acetic acid

| Sample | Sodium acetate anhydrous (SAA) | Sodium Acetate (SA) | Sodium acetate trihydrate (SAT) | Sodium diacetatte (SD) |
|---|---|---|---|---|
| Melting point (° C.) | 332.5-338 | 333-338 | 329-333 | 325-333 |
| M = Molar mass found (g/mol) | 75.57 ± 2.95 | 74.05 ± 0.39 | 121.65 ± 1.81 | 134.81 ± 12.21 |
| Mc = molar mass corrected (g/mol) | 82.03 ± 3.2 | 80.38 ± 0.42 | 132.05 ± 1.96 | 146.34 ± 13.26 |
| Expected molar mass | 82.03 | n/a | 136.08 | 142.09 |

Non-Aqueous Titration of Acetate with Perchloric Acid

The molar mass of the different salts determined by titration are shown in Table 3. The molar mass calculated for SAA matches the molar mass calculated for SA. This surprising result is consistent with the composition of SA, in terms of the ratio of acetate ion to sodium cation, is similar to that of SAA and not SD (sodium diacetate) even though, SA is prepared via half neutralization of acetic acid with sodium hydroxide.

Non Aqueous Titration of Acetic Acid Content in the Salt with Lithium Methoxide (LM)

FIG. 3 shows the titration curve of different salts and acetic acid glacial in methanol with LM used a titrant. The titration curve of both SAA and SA with LM overlaps suggesting that the two salt are the same in term of acetate ion. There is no inflexion point, whereas the titration curve of both acetic acid in methanol and SD has an inflexion point suggesting SD indeed contains acetic acid.

In Vitro Drug Release

FIG. 4 shows the release profile of TFV from different nanoformulations and Table 4 gives the value of "n" that characterized the release mechanism of the TFV from the NPs. There are a sustained release of the drug over a period of 5 days and the release mechanism is anomalous transport based on Korsmeyer Peppa model.

TABLE 4

Value of "n" for the different coated nano-formualtions using the Korsemeyer-Peppas model

| Formulation | Citrate buffer ph 4.2 | Tris Hcl buffer pH 7.51 |
|---|---|---|
| F1 | n = 0.86 ($R^2$ = 0.970) | n = 0.78 ($R^2$ = 0.991) |
| F2 | n = 0.61 ($R^2$ = 0.974) | n = 0.79 ($R^2$ = 0.998) |
| F3 | n = 0.71 ($R^2$ = 0.999) | n = 0.63 ($R^2$ = 0.994) |

$R^2$ represents the fit of the model, n indicates the likely release mechanism.

FTIR Spectrum Analysis

FIG. 5. shows the FTIR result of the individual component (A=TFV, B=TPP, C=chitosan) used for the preparation of TFV loaded chitosan NPs as well as the three physical mixtures (D=P1, E=P2, F=P3). P1, P2, and P3 are the physical mixtures of the three main ingredients TFV (2 mg, 4 mg and 6 mg respectively), TPP (8 mg) and chitosan (40 mg) respectively. As shown in FIG. 5, The FTIR spectrums of P1, P2, and P3 show the presence of the individual component TFV, TPP and chitosan respectively. The FTIR spectrum of G=SAA is identical of the FTIR spectrum of H=SA. The FTIR spectrums of I="blank", J=F1, K=F2, and L=F3 are identical to the spectrum of the pure salt SA after lyophilization confirming the deposition of the salt on the surface of the NPs.

X-Ray Powder Diffractometric (XRD)

FIG. 6. shows the XRD pattern of the individual component (A=Tenofovir, B=TPP, C=chitosan) used for the preparation of Tenofovir loaded chitosan NPs as well as the three physical mixtures (D=P1, E=P2, F=P3). P1, P2, and P3 respectively. As shown in FIG. 6, The XRD pattern of P1, P2, and P3 showed the presence of the individual components Tenofovir, TPP and chitosan, respectively. The XRD pattern of G=SAA qualitatively matches that of H=SA. The XRD pattern of I="blank", J=F1, K=F2, and L=F3 match the pattern of the pure salt SA after lyophilization confirming deposition of the salt on the surface of the NPs.

Nanoformulation Cytotoxicity Assessment

Assessment of Cell Membrane Integrity in Treated RAW 264.7 Cells

FIG. 7 shows the membrane integrity of cells treated. The NPs are investigated for their effect on plasma membrane integrity using the neutral red (NR) assay, which distinguishes between viable, damaged, or dead cells. The specific accumulation of NR in lysosomes is dependent on an intact plasma membrane and functioning lysosomes. As indicated in FIG. 7, the four nanoformulations (F0, F1, F2, and F3) did not compromise the cell membrane integrity of the macrophages, as no significant disruption of NR cell uptake was observed, based on both ANOVA test and all pairs Tukey's HSD test. In contrast, upon exposure to the positive control (LPS), a dramatic loss of cell membrane integrity was observed (~81%, p<0.0001).

Assessment of Mitochondrial Activity in Treated RAW 264.7 Cells

Figure 8:
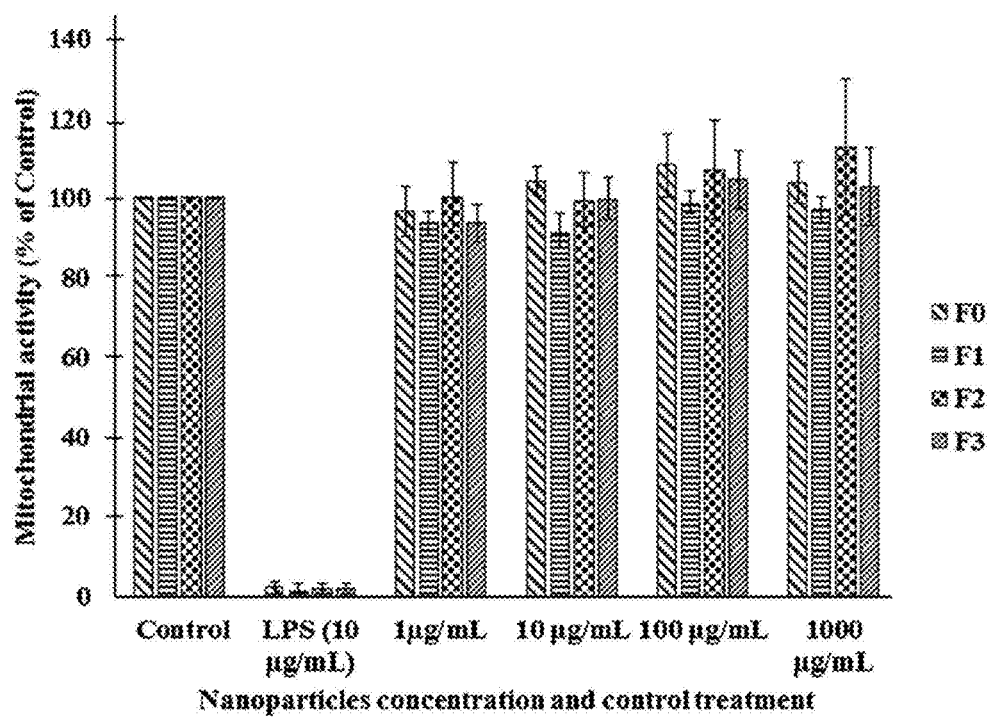
FIG. 8. Percent RAW 264.7 cell mitochondrial activity (% control) treated with different NPs formulations FO (pattern fill, downward diagonal), F 1 (pattern fill, horizontal), F2 (pattern fill, sphere), and F3 (pattern fill, upward diagonal), respectively, (n=3).

FIG. 8 shows the mitochondrial activity of treated cells. The resazurin assay was used to evaluate mitochondrial activity. As illustrated in FIG. 8, following 24 hours exposure, the four nanoformulations (F0, F1, F2, and F3) did not cause any impairment of mitochondrial activity in the macrophages based on both ANOVA test and all pairs Tukey's HSD test. In contrast, the positive control (LPS) induced a dramatic decrease of mitochondrial activity by ~98% (P<0.0001).

Assessment of No Production in Treated RAW 264.7 Cells

FIG. 9 indicates the level of nitric oxide released from the treated cells. The NPs were tested for their potential to induce cellular NO production which is considered a sensitive biomarker for pro-inflammatory response associated with macrophage activation. The secretion of NO by RAW 264.7 cells in the supernatant culture medium is quantified, by measuring nitrites accumulation. As shown in FIG. 9, in the absence of a stimulator the basal level of nitrites in RAW 264.7 cells were 7.4-8.27 µM. In response to 24 hours stimulation by LPS, inducible NO Synthase (iNOS) is appears to be strongly induced in the macrophages as evidenced by the significant accumulation of nitrites in cell culture supernatant 22.54-25.50 µM (see FIG. 9), based on ANOVA test and all pairs Tukey's HSD test (P<0.0001). For each of the four nanoformulations (F0, F1, F2, and F3), there was no significant effect on nitrite production compared to the basal level (FIG. 9).

Assessment of IL-1A, IL-1B and IL-6 and IL-7 Production in Treated RAW 264.7 Cells FIG. 10 shows IL-1α, IL-1β and IL-6 released from the cell. The NPs are tested for their potential action in inducing cytokine released which is considered as a sensitive biomarker for pro-inflammatory response associated to macrophage activation. IL-7 released was assessed to elucidate whether or not the NPs facilitates HIV transmission through its significant release after 24 hours exposition to the NPs. As shown in FIG. 10, in the absence of a stimulator the basal level of cytokine released was 5.28 pg/ml, 2.35 pg/mL and 0.70 pg/mL and 1.59 pg/mL respectively for IL-1α, IL-1β, IL-6 and IL-7. In response to 24 hours stimulation by LPS, significant amount of cytokine was released from the macrophages as evidenced by the significant accumulation of IL-1α, IL-1β and IL-6 in cell culture supernatant, 64 pg/mL, 34.73 pg/mL, 55790.25 pg/mL, and 2.33 pg/mL respectively for IL-1α, IL-1β, IL-6, and IL-7 (FIG. 10), based on ANOVA test and all pairs Tukey's HSD test (P<0.0001). As for the four nanoformulations (F0, F1, F2, and F3), there were no significant production of cytokine compared to the basal level (see FIG. 10).

EXAMPLE

Figure 11:
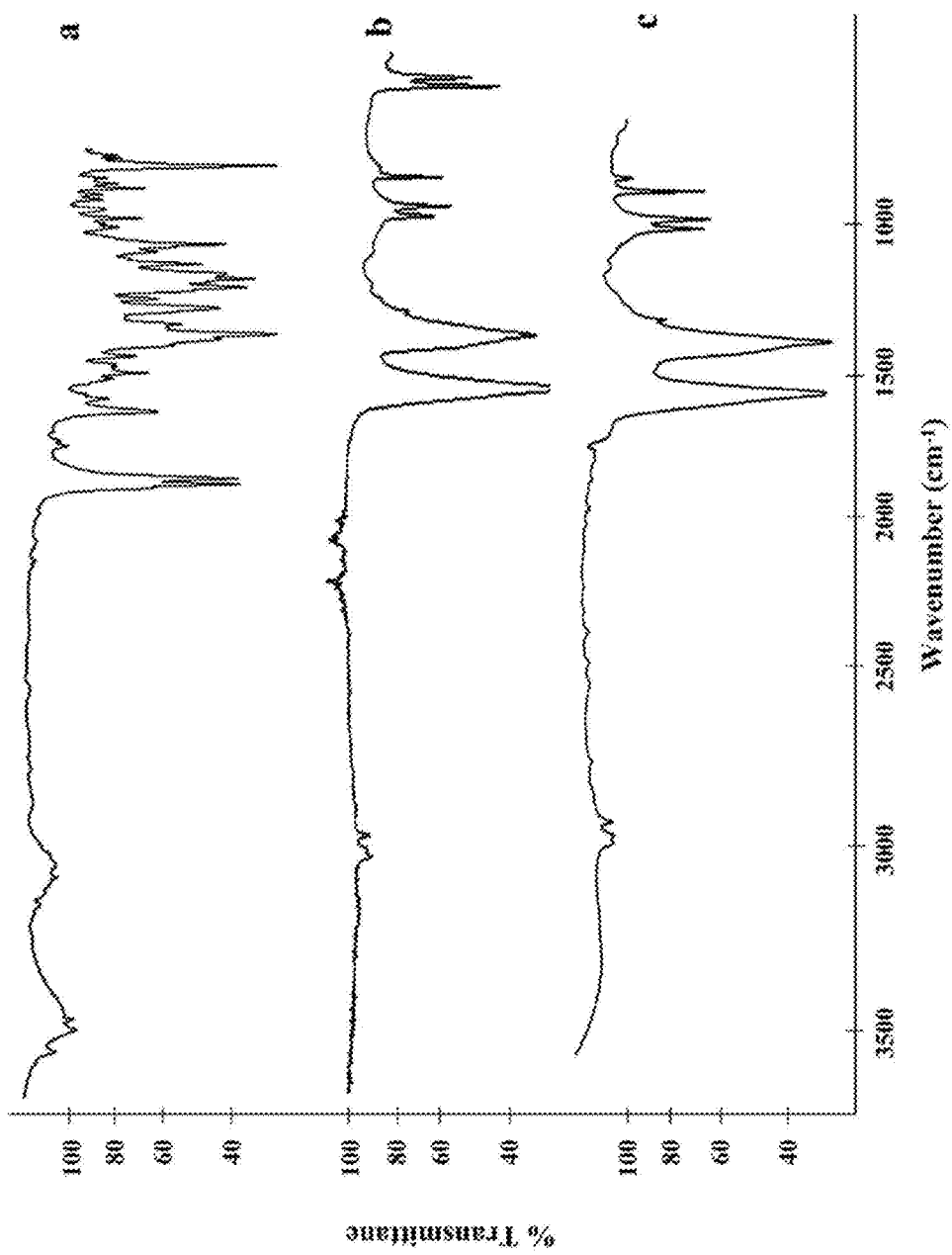
FIG. 11. FTIR spectrum of native docetaxel (a), pure sodium acetate (b), and sodium acetate coated docetaxel (c), respectively.
Figure 12:
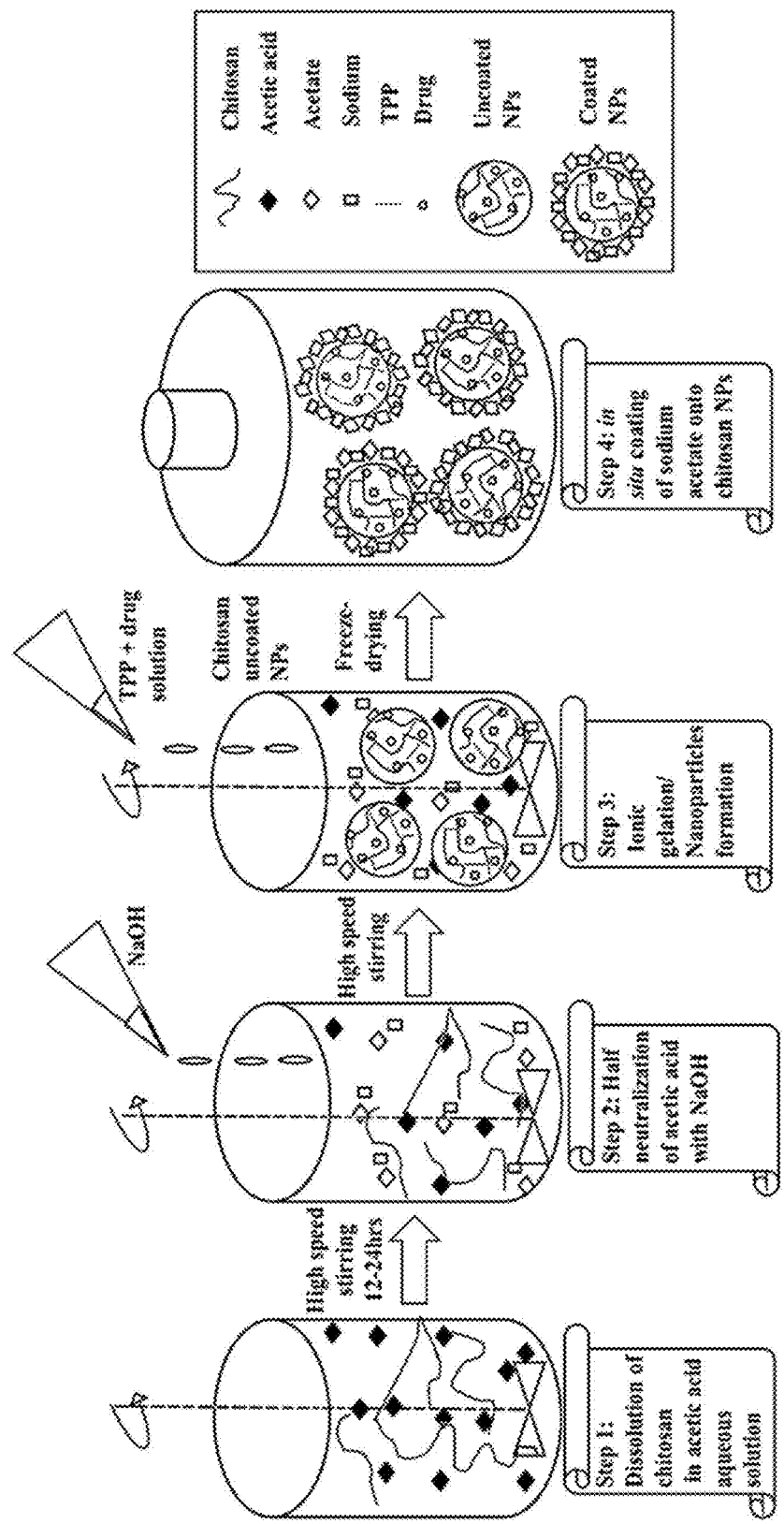
FIG. 12. Schematic representation of the process of coating chitosan nanoparticle encapsulate drug with sodium acetate salt.

Docetaxel (DXT) is an anti-cancer chemotherapy drug. It is a BCS II drug, having low water solubility. Acetate was generated by deprotonation of acetic acid with sodium hydroxide. Sodium hydroxide was added raising the pH of the solution to 12.30. This value is above the pKa values of both acetic acid (pKa=4.76) and DXT (PKa ~10.96). DXT (2 mg/mL) was dissolved in this aqueous solution of sodium acetate for a period of about 24 hours. After the period of about 24 hours elapsed, the solution was freeze dried. The amount of DXT that dissolved into solution from each DXT composition was measured by determining the amount of DXT in the supernatant, as measured by UV spectroscopy at 230 nm after removing undissolved material by centrifugation. Dissolution of coated DXT into acetate buffer at a final pH of about 7 followed by centrifugation yielded the supernatant. Native DXT (uncoated) dissolved into acetate buffer at the same pH was used as a control. The physico-chemical properties of SA coated DXT are characterized by FTIR analysis (see FIG. 11) and melting point respectively. FTIR shows that the DXT freeze-dried in the presence of sodium acetate is consistent with DXT coated with SA. The MP of pure SA, native DXT and coated DXT are 333-338° C., 177-180° C. and, 326-327° C., respectively. SA coated DXT is thermally more stable compared to non-coated DXT. It is believed that this higher stability is due to the protection of DTX by the SA coating or shell. As determined by the method described above, the solubility of uncoated DXT is low, about 11.8±0.7 µg/mL. Surprisingly, the solubility of the coated DXT, measured by the same method is 3050±15 µg/mL. There is an unexpected increase of the solubility of DXT by ~260 times. It is believed that this increased solubility is due the coating of the freeze-dried DXT with sodium acetate and/or the hydrotropic properties of sodium acetate.

What is claimed is:

1. A process for improving the aqueous solubility of a material in a first aqueous solution wherein the material has a water solubility at a pH of about 6 to about 8 selected from the group consisting of about 1 mg/mL to about 500 μg/mL, about 400 μg/mL to about 300 μg/mL, about 300 μg/mL to about 200 μg/mL, about 200 μg/mL to about 100 μg/mL to, about 100 μg/mL to about 50 μg/mL, about 50 μg/mL to about 25 μg/mL, about 25 μg/mL to about 10 μg/mL, and about 10 μg/mL to about 1 μg/mL, the process comprising:

(a) forming a second aqueous mixture comprising nanoparticles of the material and one or more acetate salts selected from the group consisting of LiOAc, NaOAc, KOAc, and CsOAc, where the acetate salt is formed in situ from acetic acid and an added base containing an appropriate counter ion; and (b) freeze drying the second aqueous mixture from (a) to yield nanoparticles of the material coated with a shell of the acetate salt wherein the material has improved aqueous solubility when the solid is mixed with the first aqueous solution.

2. The process of claim 1 wherein the material comprises a bioactive compound.

3. The process of claim 2 wherein the material comprises the bioactive compound and a biodegradable polymer selected from the group consisting of poly(L-lactide) (PLLA), poly(D,L-lactide) (PDLLA), poly(lactic-co-glycolic acid) (PLGA), (poly)caprolactone (PCL), and chitosan.

4. The process of claim 3 wherein the bioactive compound is a pharmaceutical agent.

5. The process of claim 4 wherein the pharmaceutical agent is selected from the group consisting of antibacterials, antivirals, and cancer drugs.

6. The process of claim 3 wherein the bioactive compound is encapsulated by the biodegradable polymer.

7. A composition comprising a material prepared by the process of claim 1.

8. The process of claim 1 wherein the material has a log P value of about 1 to about 2, about 2 to about 3, about 3 to about 4, about 4 to about 5, or about 5 to about 8.

9. The process of claim 8 wherein the material has a log P of about 2 to about 3.

10. The process of claim 8 wherein the material has a log P of about 3 to about 4.

11. The process of claim 1 wherein the shell of acetate salt has a thickness that is about 5% to about 7.5%, about 5% to about 10%, about 10% to about 15%, about 10% to about 20%, about 15% to about 25%, about 25% to about 50%, or about 50% to about 100% of the diameter of the nanoparticles.

12. The process of claim 4 wherein the material is docetaxel.

* * * * *